US009119828B2

(12) United States Patent
 Alving

(10) Patent No.: US 9,119,828 B2
(45) Date of Patent: Sep. 1, 2015

(54) ANTIBODIES WITH SIMULTANEOUS SUBSITE SPECIFICITIES TO PROTEIN AND LIPID EPITOPES

(75) Inventor: Carl R. Alving, Bethesda, MD (US)

(73) Assignee: The United States of America as represented by The Secretary of the Army, Washington, DC (US)

( * ) Notice: Subject to any disclaimer, the term of this patent is extended or adjusted under 35 U.S.C. 154(b) by 25 days.

(21) Appl. No.: 11/525,574

(22) Filed: Sep. 22, 2006

(65) Prior Publication Data

US 2007/0072225 A1    Mar. 29, 2007

Related U.S. Application Data

(60) Provisional application No. 60/722,084, filed on Sep. 23, 2005.

(51) Int. Cl.
 *A61K 39/21*  (2006.01)
 *C07K 16/18*  (2006.01)
 *C07K 16/10*  (2006.01)
 *C07K 16/46*  (2006.01)

(52) U.S. Cl.
 CPC ............ *A61K 39/21* (2013.01); *C07K 16/1063* (2013.01); *C07K 16/18* (2013.01); *C07K 16/468* (2013.01)

(58) Field of Classification Search
 None
 See application file for complete search history.

(56) References Cited

U.S. PATENT DOCUMENTS

| 5,695,927 | A * | 12/1997 | Masuho et al. ................ 435/5 |
| 5,831,034 | A * | 11/1998 | Katinger et al. ......... 530/388.35 |
| 6,214,984 | B1 * | 4/2001 | Zapata ........................ 536/23.4 |
| 2004/0033487 | A1 * | 2/2004 | Nabel et al. ..................... 435/5 |

OTHER PUBLICATIONS

Ofek et al., Journal of Virology, 2004, vol. 78, p. 10724-10737.*
Richards et al. Immunology and Cell Biology, 2004, vol. 82, p. 531-538.*
Stiegler et al. AIDS Research and Human Retroviruses, 2001, vol. 17, p. 1757-1765.*
Karasavvas et al. Biochemical and Biophysical Communications, 2008, vol. 366, p. 982-987.*
Verma et al. (Infection and Immunity, 1992, vol. 60, p. 2438-2444.*
Manes et al. (EMBO, 2000, p. 1-7).*
Verma et al. (Infection and Immunity, 1992, vol. 60, p. 2438-2444 of record on Jul. 20, 2009) i.*
Richards et al. (Immunology and Cell Biology, 2004, vol. 82, p. 531-538 in IDS on Oct. 24, 2007.*
Haynes et al. (Science, Jun. 2005, vol. 308, p. 1906-1908 in IDS on Oct. 24, 2007).*

(Continued)

*Primary Examiner* — Agnieszka Boesen
(74) *Attorney, Agent, or Firm* — Caroline Nash; Nash & Titus, LLC; Elizabeth Arwine

(57) ABSTRACT

Antibodies and method of making antibodies, either monoclonal or polyclonal wherein said antibodies have dual or multi-specific binding capacity to more than one type of antigenic epitope. The antibodies have simultaneous or independent recognition subsites to each of the epitopes. Antigenic epitopes include lipids, peptides, proteins, amino acid sequences, sugars and carbohydrates. Monoclonal antibodies and a method of making monoclonal antibodies of the invention include monoclonal antibodies that are broadly neutralizing to HIV-1 or other envelop viruses wherein the monoclonal antibody has subsites that simultaneously recognize protein and lipid epitopes from the virus.

6 Claims, 10 Drawing Sheets

(56) References Cited

OTHER PUBLICATIONS

Beck et al. Retrovirology, 2009) 1 page.*
Stoller, et al., "Cross-reaction of nucleic acids with monoclonal antibodies to phosphatidlyinositol phosphate and cholesterol." Molecular Immunology, Jan. 1989, vol. 26, No. 1, pp. 73-79.
Bichards Roberta, et al., "Liposome stabilized oil in water emulsions as adjuvants; increased emulsion stability promotes induction of cytotoxic T lymphocytes against an HIV envelope antigen" Immunology and Cell Biology, Oct. 2004, vol. 82, No. 5, pp. 531-538.
Hayes, et al., "Cardiolipin polyspecific autoreactivity in two broadly neutralizing HIV-1 antibodies", Science, Jun. 24, 2005, vol. 308, No. 5730, pag, 1906-1908.
Nabel, "Immunology. Close to the edge: neutralizing the HIV-1 envelope" Science American Association for the Advancement of Science, US, vol. 308, No. 5730, Jun. 24, 2005, pp. 1878-1879.
Wasef, et al., "Phosphate binding specificities of monoclonal antibodies against phosphoinositides in liposomes." Molecular Immunology, Oct. 1984, vol. 21, No. 10, pp. 863-868.
Kouts, et al., "Immunization of a rabbit with beta 2-glycoprotein I induces charge dependent crossreactive antibodies that bind anionic phospholipids and have similar reactivity as autoimmune anti-phospholipid antibodies" Journal of Immunology, The Wiliams and Wilkins Co. Baltimore, US, vol. 155, No. 2, 1995, pp. 958-966.
Rollman, et al, "Multi-subtype gp160 DNA immunization induces broadly neutralizing anti-HIV antibodies" Gene Therapy MacMillan Press Ltd., vol. 11, No. 14, Jul. 2004, pp. 1146-1154.
Alving, "Antibodies to liposomes phospholipids and phosphate esters." Chemistry and Physics of Lipids, Jun.-Jul. 1986, vol. 40, No. 2-4, pp. 303-314.
Zolton, et al., Membrane-specific antibodies induced by liposomes can simultaneously bind to HIV-1 protein, peptide, and membrane lipid epitopes, Journal of Drug Targeting, 2008; 00(0) 1-8.
McElrath, Cancer Biology, vol. 6, pp. 375-385 (1995) Selection of potent immunological adjuvants for vaccine construction.
Nabel, Close to the Edge Neutralizing the HIV-1 Envelope, Science, vol. 308, pp. 1878-1879 (2005).
Haynes, et al., HIV-1 Hides an Achilles' Heel in Virion Lipids, Immunity 28, pp. 10-12 (2008).
Baqar, S., Safety and immunogenicity of a prototype oral whole-cell killed *Campylobacter* vaccine . . . , Vaccine, vol. 13, No. 1, pp. 22-28 (1995).
Ofek G, et al., Structure and mechanistic analysis of the anti-human immunodeficiency virus type 1 antibody 2F5 in complex with its gp41 epitope, Journal of virology, the American soc. of microbiol. vol. 78, No. 19, (2004).
McAlarney et al., Specificity and Cross-reactivity anti-galactocerebroside antibodies, Immunological investigations, Marcel Dekker, NY, NY, vol. 24, No. 4, 1995, p. 595-606.
Alving, et al., Lipid a and liposomes containing lipid a as antigens and adjuvants, Vaccine, 2008, vol. 26, No. 24, p. 3036-3045.
Liposome Technology, 2nd Edition, vo. III, Interactions of Liposomes with Biological Milieu, CRC Press, pp. 317-343 (1993).
Handbook of Lipid Research, Small, Donald, Plenum Press, NY, vol. 4 pp. 48-50 (1986).
Swartz, et al., Antibodies to cholesterol, Proc. Natl. Acad, Sci USA, vol. 85, pp. 1902-1906 (Mar. 1988).
Alving, et al., HIV-1, lipid refts, and antibodies to liposomes: implications for anti-viral-neutralizing antibodies (Review), Molecular Membrane Biology, 23(6) (Nov.-Dec. 2006).
Alving, et al., Cholesterol-Dependent Humand Complement Activation Resulting in Damage to Liposomal Model Membranes, The Journal of Immunology, vol. 118, No. 1, pp. 342-347, (Jan. 1977).
Alving, et al., Lupus anticoagulant activities of murine monoclonal antibodies to liposomal phosphatidylinositol phosphate, Chin. exp. Immunol. 69, pp. 403-408 (1987).
Matyas, G.R., Standard Operating Procedure Production of Monoclonal Antobodies Fusion of Spleen Cells, Monoclonal Fusion Protocol, pp. 1-8 (date unknown).

* cited by examiner

ANTIBODIES WITH SIMULTANEOUS SUBSITE SPECIFICITIES TO PROTEIN AND LIPID EPITOPES

This invention is based on and claims priority from U.S. Provisional Application Ser. No. 60/722,084 filed Sep. 23, 2005, incorporated herein by reference.

GOVERNMENT INTEREST

The invention described herein may be manufactured, used and licensed by or for the U.S. Government.

BACKGROUND OF THE INVENTION

1. Field of the Invention

The present invention relates to a method of making dual specific antibodies. More specifically, the present invention relates to a method of making antibodies that are dual specific to both (1) amino acid sequences and (2) solid phase lipid structures. The present invention has relevance to such important subject matter as making broadly neutralizing monoclonal antibodies to HIV-1.

2. Brief Description of Related Art

One of the major barriers that have emerged in the development of an effective HIV-1 vaccine is the difficulty in obtaining neutralizing antibodies that block infection by primary isolates derived from a wide cross-section of clades (subtypes). In order to obtain broadly neutralizing or protective antibodies to HIV-1 it is necessary for antibodies to utilize antigenic epitopes (i.e., molecular recognition sites for binding of antibodies) that are conserved in the virus or that are present in the host or target cell in the regions in which the virus either buds or where binding or fusion with the virus occurs (McMichael & Hanke 2003; Burton et al. 2004). Most mammalian cells have a relatively conserved repertoire of lipids in the lipid bilayer of the plasma membrane, including glyceryl phospholipids, sphingosyl phospholipids (mainly sphingomyelin), lysophospholipids, glycosphingolipids, and cholesterol.

The human immunodeficiency virus type 1 (HIV-1) is an enveloped virus with a lipid bilayer that contains several glycoproteins that are anchored in, or closely associated with, the membrane surface. The envelope proteins have complex interactions with the lipids both on the host cells and on the target cells. The processes of budding from host cells and entry into target cells occur at sites on the plasma membrane, known as lipid rafts that represent specialized regions that are rich in cholesterol and sphingolipids. Although the envelope glycoproteins are antigenic molecules that potentially might be used for development of broadly neutralizing antibodies in a vaccine to HIV-1, the development of such antibodies that have broad specificities against primary isolates of virus have been largely thwarted to date by the ability of the envelope proteins to evade the immune system through various mechanisms.

It has been known for more than 20 years that monoclonal antibodies can have subsite specificities that simultaneously recognize different epitopes, such as simultaneous recognition of different types of carbohydrates; or combinations of carbohydrate and sulfated molecules, or carbohydrates and phosphorylated molecules. These subsites for different epitopes exist simultaneously in the same overall antigen binding site of the antibody. In our research, we have found polyclonal or monoclonal antibodies to membrane associated lipid antigens that also contain subsites that recognize unrelated phosphate or sulfated molecules as an epitope. We have also found that numerous membrane associated protein antigens have subsites that also recognize phosphate and even cross-react with phospholipids. However, this research has not produced a monoclonal antibody that is broadly neutralizing to HIV-1.

Therefore, an object of the present invention was to make antibodies that have dual specific action by recognizing, as antigens or epitopes, both (1) amino acid sequences such as proteins, peptides and polypeptides and also (2) solid phase lipid structures such as lipids, liposomes and the like so that the antibody will have greater affinity for these antigens or epitopes at the surface of target organisms or cells. The amino acid sequences and solid phase lipid structures may be from entities such as viruses, bacteria, cancer cells, hormones or any other substance that produces an immune response, wherein both (1) and (2) are capable of being recognized individually or together (i.e., simultaneously) by the antibody.

Another object of the invention was to apply this strategy to obtain antibodies that are broadly neutralizing to HIV-1 because they have subsites that recognize both protein and lipid or carbohydrate antigenic epitopes that are present either on the virus or on the budding site, receptor site, or fusion site of the plasma membrane.

In the case of HIV-1, this is necessary for the antibody to have dual specificity with the HIV-1 protein and with the plasma membrane of the host cell in the vicinity of the HIV-1 virus. In the case of other entities that produce an immune response, the antibodies will either be to the lipids themselves or to the combined lipid and amino acid sequences. The antibodies will either interfere with the entity through steric hindrance, or through conformational changes in the lipids that will interfere with the viability of the entity, or that will activate complement or other types of innate immunity as an effecter mechanism.

FIG. 4 is a schematic model of the HIV-1 putative trimeric envelope spike. The viral particle 2 is shown inserted into the plasma membrane 5. Most of the surface of gp 41 is believed to be occluded by gp120. However, the amino acid sequences of gp41 close to the membrane that have been identified as binding sites of MABs 2F5, Z13, and 4E10 have been suggested to be exposed to antibody binding (Zwick et al., 2001). IgG is shown as 20.

The invention solves the problems associated with the past lack of ability to find antibodies that are broadly neutralizing. In the case of HIV-1, the invention solves the problem by showing that patterns of plasma membrane lipids, known as lipid rafts, serve as binding sites not only for viral interactions with host and target cells, but also as lipids that might be incorporated into HIV-1 to comprise the lipid bilayer of the virus envelope and exploiting this knowledge to produce monoclonal or polyclonal antibodies that recognize these lipids as well as HIV-1 peptides. This invention will have particular relevance for HIV vaccine research and development, and for the treatment of HIV-1 and for research, vaccine development, and treatment of other enveloped viruses.

SUMMARY OF THE INVENTION

The present invention relates to a method of making dual specific antibodies. More specifically, the present invention relates to a method of making antibodies that are dual specific for binding to both (1) amino acid sequences and (2) organized lipid structures, such as lipids present in a lipid bilayer membrane.

The present invention is also directed to a method of making monoclonal antibodies by obtaining liposomes having lipid epitopes similar to those present on HIV-1 and modifying the liposomes by including an adjuvant in the liposomes, or by injecting the liposomes together with an adjuvant, and such liposomes also contain protein or peptide epitopes from HIV-1 virus. The liposomes contain lipid combinations comprising cholesterol, sphingomyelin, charged phospholipids, phosphatidylethanolamine, galactosyl ceramide, or sulfogalactosyl ceramide to name a few of the lipids from the lipid raft region of the plasma membrane. Then the liposomes are inserted into a mammal to produce monoclonal antibodies against the liposomes. The monoclonal antibodies have simultaneous recognition subsites to lipid epitopes in the liposome and to the protein of HIV-1 virus.

Other objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

The accompanying drawings show illustrative embodiments of the invention from which these and other of the objectives, novel features and advantages will be readily apparent.

DETAILED DESCRIPTION

Figure 1:
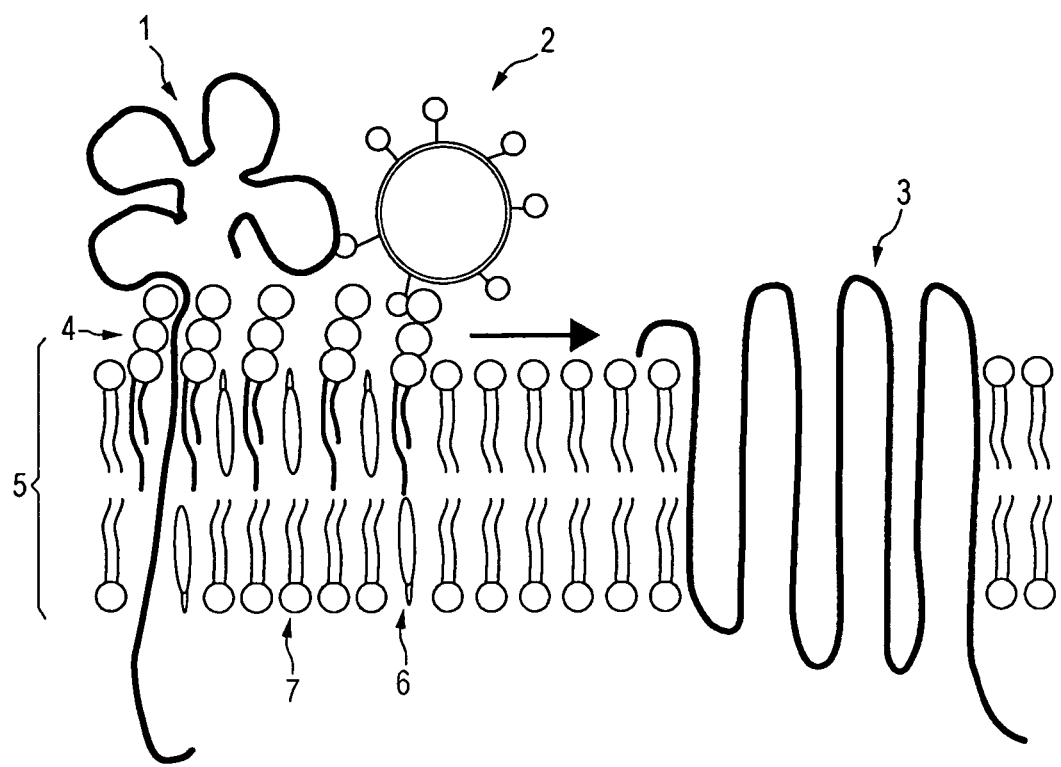
FIG. 1 is a diagram of the plasma membrane glycosphingolipid microdomains as preferential sites of formation of the HIV-1 fusion complex.

The method of the present invention applies to the making of monoclonal antibodies and antibodies that have dual specificity and are broadly neutralizing. The dual specificity is obtained by making monoclonal antibodies and polyclonal antibodies that recognize both (1) amino acid sequences such as amino acid sequences of one or more of proteins, peptides and polypeptides and (2) organized lipid domains, including solid phase lipid structures such as one or more types of lipids, liposomes or the like.

The method involves obtaining an organized lipid structure that has lipid properties that resemble or mimic the lipids found in a particular entity. Entities include viruses, bacteria, hormones, fungi, protozoa, cancer cells, or anything else that produces an antibody when introduced to a mammal. Then added to the organized lipid structure are amino acid sequences that resemble or mimic amino acid sequences from peptide epitopes, polypeptides, proteins or the like. This modified lipid structure is then inserted into a mammal to induce an immune response which is the production of antibodies that are dual specific to the lipids and amino acid sequences in the modified organized lipid structure. Optionally and preferred is to also incorporate an adjuvant into the modified solid phase lipid structure.

Materials and Methods:

HIV-1

Murine antibodies were made by injecting mice with liposomes containing lipid A and protein from HIV-1 (either gp 160, gp 120, gp140, or gp 41). The preferred antibody is a monoclonal antibody.

Preparation of Liposomes:

The liposomes were prepared by making a liposome containing one or more lipids found in the lipid bilayer of the plasma membrane of the host cell in the region of the lipid raft or one or more types of lipids normally found in HIV-1. Then the adjuvant, lipid A and the protein from HIV-1 were inserted into the liposome. The liposomes contain lipid combinations comprising one or more of cholesterol, sphingomyelin, charged phospholipids, phosphatidylethanolamine, galactosyl ceramide, or sulfogalactosyl ceramide to name a few of the lipids from the lipid raft region of the plasma membrane. The lipid A and the protein are either attached to the surface of the liposomes, or intercalated into the liposomal membrane bilayer, or encapsulated in the aqueous spaces inside the liposome The liposomes are easily prepared using methods known in the art and as found in U.S. Pat. Nos. 5,888,519, 6,093,406, incorporated herein in their entirety by reference. The following general methods for manufacturing liposomes have been published, and are incorporated in their entirety by reference:

Swartz, Jr., G. M., Gentry, M. K., Amende, L. M., Blanchette-Mackie, E. J. and Alving, C. R. Antibodies to cholesterol. Proceedings of the National Academy of Sciences, U.S.A. 85 1902-1906 (1988).

and,

Alving, C. R., Shichijo, S., Mattsby-Baltzer, I., Richards, R. L. and Wassef, N. M. Preparation and use of liposomes in immunological studies. Liposome Technology, vol. 3, (Second Edition), (Gregoriadis, G., ed.), CRC Press, Inc., Boca Raton, Fla., pp. 317-343 (1993). Some specific details are given below. This describes the preferred liposome composition.

Lipids from Avanti (dimyristol-phosphatidylcholine (DMPC), dimyristol-phosphatidylglycerol (DMPG), and cholesterol) dissolved in distilled chloroform were added to 50 ml pear-shaped flasks in 9:1:25 (DMPC:DMPG:cholesterol) molar ratio along with Lipid A (Avanti) in a final concentration of 200 µg/ml. Lipids were deposited as a thin film under 0.1 kPa vacuum at 40° C. on a rotaevaporator with 230 rpm. The lipids were then dried overnight in desiccator. The high cholesterol (71%) liposomes were formed in distilled water then lyophilized for 24 hours. Gp140 protein oh HIVIIIB (The Biotech Source) in PBS was added to the lipids to yield 50 mM phospholipid suspensions, forming multilamellar liposomes with 100 µg/ml incorporated HIV glycoprotein. All suspensions were stored at 40° C. until injection.

Liposomes within the present invention can be prepared in accordance with known laboratory techniques. In one preferred embodiment, liposomes can be made by mixing together the lipids to be used, including lipid A, in a desired proportion in a container, e.g, a glass pear-shaped flask, having a volume ten times greater than the volume of the anticipated suspension of liposomes. Using a rotary evaporator, the solvent is removed at approximately 40° C. under negative pressure. The vacuum obtained from a filter pump aspirator attached to a water faucet may be used. The solvent normally is removed within about 2 to 5 minutes. The composition can be dried further in a desiccator under vacuum. The dried lipids are generally discarded after about 1 week because of its tendency to deteriorate with time.

The dried lipids can be hydrated at approximately 30 mM phospholipid in sterile, pyrogen-free water by shaking until all the lipid film is off the glass. The aqueous liposomes can be then separated into aliquots, each placed in a vaccine vial, lyophilized and sealed under vacuum.

In the alternative, liposomes can be prepared in accordance with other known laboratory procedures, e.g., the method of Bangham et al., J. Mol. Biol. 13: 238-52 (1965), the contents of which are incorporated herein by reference; the method of Gregoriadis, as described in "Liposomes" in DRUG CARRIERS IN BIOLOGY AND MEDICINE, pp. 287-341 (G. Gregoriadis ed. 1979), the contents of which are incorporated herein by reference; the method of Deamer and Uster as described in "Liposome Preparation: Methods and Mechanisms" in LIPOSOMES (M. Ostro ed. 1983), the contents of which are incorporated by reference; and the reverse-phase evaporation method as described by Szoka, Jr. and Papahadjopoulos, in "Procedure for Preparation of Liposomes with Large Internal Aqueous space and High Capture by Reverse-Phase Evaporation," Proc. Natl. Acad. Sci. USA 75: 4194-98 (1978). The aforementioned methods differ in their respective abilities to entrap aqueous material and their respective aqueous space-to-lipid ratios.

Synthetic lipid A can be purchased from available commercial sources, e.g., Calbiochem-Behring (La Jolla, Calif.), List Biological Laboratories, Inc. (Campbell, Calif.) and Corixa (formerly, Ribi Immunochem Research, Inc.) (Hamilton, Mont.). LPS is similarly available from commercial sources, e.g., Difco (Detroit, Mich.), List Biological Laboratories, Inc. and Corixa. When the lipid A is inserted into the liposome, the toxic portion of lipid A which usually causes fever is embedded in the liposome. Therefore, lipid A does not cause a toxic response and has been found not to be dangerous. The inventor found that when lipid A is embedded in the liposome and injected in mice, rabbits, or humans, it sends out a signal to the immune system. The immune system is then immobilized to send out an immune response to anything that is near the lipid A. In the preferred embodiment of the invention, the immune system sends out a response that attacks HIV-1 by producing antibodies that simultaneously recognize lipid epitopes and HIV-1 protein or peptide epitopes. Lipid A is used as an adjuvant, however, other adjuvants that are known to induce an immune response may also be incorporated into the liposome.

The liposomes contain a variety of lipid compositions that mimic the known lipid composition of HIV-1 and that also include lipid A as a liposomal adjuvant. An example of such a liposome composition can contain one or more of phosphatidyl choline (PC), phosphatidylethanolamine (PE), sphingomyelin (SM), phosphatidylserine (PS), Phosphatidylinositol-4-phosphate (PIP) and cholesterol in the approximate concentrations found in HIV-1 isolated as described in Aloia et al., *Lipid composition and fluidity of the human immunodeficiency virus envelope and host cell plasma membrane*, Proc. Natl. Acad. Sci. USA 1993; 90:5181-5185. Cholesterol can also be increased in the liposomes to optimize the induction of antibodies to cholesterol. The liposomes can also contain galactosyl ceramide (GalCer), sulfogalactosyl ceramide (SGalCer), ceramide trihexoside (CTH), ganglioside GM1 (GM1), or ganglioside GM3 (GM3), and phosphatidyl glycerol. These synthetic liposomes have lipids that mimic the lipid raft of the plasma membrane and which are also incorporated into the structure of HIV-1

Included within the scope of the present invention is changing or incorporating of one or more of the different lipids mentioned above in the liposome in order to achieve a desired result. Any of a combination of the lipids mentioned, or similar types of lipids, or synthetics, are within the scope of the invention.

Incorporation of HIV-1 Protein into Liposomes

As indicated above, in addition to the above lipids, the liposomes also contain relevant HIV-1 protein or peptide epitopes that bind to or interact with lipids, including gp160, gp140, or gp41 from HIV-1 envelope. The liposomes may also contain nef, either alone or with env antigens, because nef, is known to react with the lipid bilayer particularly in association with cholesterol. It is generally found that the amino acid sequences that are present above the transmembrane sequences of gp41 are highly conserved, and the lipids themselves are highly conserved.

HIV-1 is a spherical, enveloped RNA retrovirus, a lentivirus that fuses with the plasma membrane of a host cell to insert its genomic RNA. The envelope of HIV-1 contains a lipid bilayer that is associated with two loosely bound glycoproteins, gp120 and gp41. These proteins are created during intracellular virus assembly when a precursor protein, gp160, is cleaved to form gp120 and gp41 (FIG. 1A). The gp41 is a trimeric transmembrane protein that is anchored in the lipid bilayer, and during viral maturation and budding the intraviral end of gp41 is bound to sites located on an N-terminal myristoylated matrix protein (p17) (Yu et al. 1992; Freed & Martin 1995; Hill et al. 1996). As with other enveloped viruses, the lipid composition of the virus is largely reflective of the composition of lipid rafts present in the plasma membrane of the host cell (Aloia et al. 1988 and 1993).

Cells that become infected with HIV-1 undergo cytopathological effects leading to apoptosis. This may initially occur because arginine residues on the C terminal end of gp41 (fusion peptide) electrostatically bind to phosphatidylserine (PS) or PG or other charged phospholipids on the inner lamella of the plasma membrane of the target cell. The interactions of the C terminus of gp41 with PS or PG results in the formation of a lipidic pore, or causes other lipid membrane changes, leading to cellular permeability, cytopathology, apoptosis with movement of PS from the inner lamella of the lipid bilayer to the outer lamella, and death (Chernomordik et al., 1994; Trommeshauser and Galla, 1998; Trommeshauser et al., 2000). After the subsequent acquisition of viral phospholipids from the host cell plasma membrane by the budding virus, the resultant viral lipid bilayer resembles that of apoptotic cells in that PS is present on the outer lamella of the budded viral bilayer (Callahan et al., 2003).

Protein is incorporated into the liposomes when it is included in the aqueous solution that is used to disperse the dried lipids. The liposomes form automatically and automatically enclose a volume of the aqueous protein solution that was used to disperse the liposomes.

Monoclonal Antibody Production

Monoclonal antibodies were made to the liposomes of the invention by using techniques well known in the art for making monoclonal antibodies and as found in U.S. Pat. Nos. 4,885,256 and 6,900,025, incorporated by reference. Monoclonal antibodies were produced that have subsite specificities both for lipid and amino acid epitopes and that will bind simultaneously to the lipids and the lipid-associated protein.

Methods for producing and obtaining an antibody are well known by those skilled in the art. An exemplary method includes immunizing any animal capable of mounting a usable immune response to the antigen, such as a mouse, rat, goat sheep, rabbit or other suitable mammal. In the case of a monoclonal antibody, antibody producing cells of the immunized animal may be fused with "immortal" or "immortalized" human or animal cells to obtain a hybridoma which produces the antibody. If desired, the genes encoding one or more of the immunoglobulin chains may be cloned so that the antibody may be produced in different host cells, and if desired, the genes may be mutated so as to alter the sequence and hence the immunological characteristics of the antibody produced. Fragments of binding agents, may be obtained by conventional techniques, such as by proteolytic digestion of the binding agent using pepsin, papain, or the like; or by recombinant DNA techniques in which DNA encoding the desired fragment is cloned and expressed in a variety of hosts. Irradiating any of the foregoing entities, e.g., by ultraviolet light will enhance the immune response to a multi-epitopic antigen under similar conditions. Various binding agents, antibodies, antigens, and methods for preparing, isolating, and using the binding agents are described in U.S. Pat. No. 4,471,057 (Koprowski), U.S. Pat. No. 5,075,218 (Jette, et al.), U.S. Pat. No. 5,506,343 (Fufe), and U.S. Pat. No. 5,683,674 (Taylor-Papadimitriou, et al), all incorporated herein by reference. Furthermore, many of these antibodies are commercially available from Centocor, Abbott Laboratories, Commissariat a L'Energie Atomique, Hoffman-LaRoche, Inc., Sorin Biomedica, and FujiRebio.

Immunization of Mice

The immunization procedure was performed by Biocon Inc. followed the company's approved protocol. The animal handling, quarantine measures, monitoring and vaccination of mice were used with maximal safety and minimal pain.

Liposomes were mixed with Freud's adjuvant for immunization. The group size was 5 animals per immunization. They were ear tagged and prebled after they were released from quarantine. The animals were immunized by intraperitoneal route (IP). Two weeks after immunization one animal was selected on the basis of the ELISA data screening for the antibodies against to lipids and gp140 protein. The animal was anesthetized, and terminally bled by cardiac puncture. The spleen was removed and processed for fusion with myeloma cells. The remaining 4 mice were boosted at week 3 by the IP with the same liposomal antigen formulation. They were bled at week 5, and the sera were assayed for antibodies to the antigens. The best responsive mouse was selected and immunized by the IV route. Four days later, the animal was anesthetized and terminally bled by cardiac puncture. The spleen was removed and processed for making hybridomas. The remaining mice were held for 30 days in order to determine if the production of monoclonal antibodies was successful.

Making Hybridomas

The protocol of "Standard Operating Procedure Production of Monoclonal Antibodies Fusion of Spleen Cells" was followed, relevant portions as follows and is incorporated by reference in its entirety:

Procedure assumes that Balb/c mice have been immunized and boosted with antigen. 3-4 days prior to fusion one mouse has been given an IV boost with antigen.

Materials

Cells: Fusion partner cell line—P3X63Ag8U.1 (X63)

Media and Additives:
1. Dulbecco's Modified Eagle's Medium with 4.5 g glucose (DMEM)
2. L-glutamine (200 mM) or GlutMax
3. Sodium pyuvate (100 mM)
4. MEM Non Essential Amino Acids (100×) (NEAA)
5. Penicillin-Streptomycin (10,000 units Penicillin/10,000 µg Streptomycin)
6. Fetal bovine serum—heat inactivated (FBS)
7. Hypoxanthine/Thymidine (100×) (HT)
8. Hypoxanthine/Aminopeterin/Thymidine (50×) (HAT)
9. Polyethylene glycol 4000 (Sterile and tissue culture tested is best from ATCC)
10. Typan blue
11. Hank's balance salts solution without calcium or magnesium Plasticware (Sterile):

Pipets—1, 5, 10, 25 and 50 ml, 96-well flat bottom tissue culture plates, Flasks—75 and 150 or 175 $cm^2$. Tubes—15 and 50 ml screw cap tubes, Syringes—3 or 5 ml, Petri dishes 6 cm diameter, Transfer pipets, Yellow pipet tips, Basins, Filters—1 L, 500 and 100 ml; bottle type with PES membrane Equipment:

Waterbath set at 37 C, Tabletop centrifuge set at room temperature ~25 C, Autoclave, Hot plate, Microscope—bright field for counting cells, Microscope—inverter, phase contrast for observing cultured cells, Multi-channel pipettor—12 place 50-250 or 300 µl, Pipet-aid, Biological safety cabinet Other:

Hemocytometer, 500 ml glass bottle to autoclave DI water, Screen mesh for spleens—sterile, autoclaved, Forceps—small, sterile, autoclave, Scissors—small, iris type, Test tube rack, 250 ml glass beaker, Timer with seconds, 70% Isopropanol in a spray bottle, Preparation of Media Media is prepares in a tissue culture filter apparatus. Some DMEM (~70% of what is required) is added to the filter. The additives are added using an appropriate pipet. DMEM is added to approximately the final volume. The vacuum is applied. After the media goes through the filter, the filter is discarded and the lid is placed on the bottle. Media is good for approximately 1 month at 4 C.

Media should be at 37 C when used.

DMEM (serum-free): (Used for washing spleen and myeloma cells and during the fusion.) 250 ml/fusion DMEM—235 ml, Glutamine—5 ml, Sodium pyruvate—2.5 ml, NEAA—2.5 ml, Penicillin/Streptomycin—2.5 ml, HT—2.5 ml DMEM-HT: (Used for growth of myeloma cells) 1 L DMEM—850 ml, FBS—100 ml, Glutamine—10 ml, Sodium pyruvate—10 ml, NEAA—10 ml, Penicillin/Streptomycin—10 ml, HT—10 ml DMEM—20% FBS-HT: (Used for growth of myeloma cells) 100 ml DMEM—75 ml, FBS—20 ml, Glutamine—2 ml, Sodium pyruvate—1 ml, NEAA—1 ml, Penicillin/Streptomycin—1 ml, HT—1 ml DMEM-HAT: (Used for growth of myeloma cells and the first day after fusion) 1 L DMEM—730 ml, FBS—200 ml, Glutamine—20 ml, Sodium pyruvate—10 ml, NEAA—10 ml, Penicillin/Streptomycin—10 ml, HAT—20 ml Steriled-filtered water 1 L—Needed during fusion.

Propagation of Myeloma Cell—X63
1. Place 30 ml of DMEM-HT in a 50 ml tube.
2. Remove X63 cells from liquid nitrogen.

3. Rapid thaw X63 cells by placing them in a 37 C waterbath.
4. Spray with vial 70% isopropanol and place in BSC.
5. After drying, open vial using a 2 ml pipet transfer the contents to the centrifuge tube in step 1.
6. Centrifuge at 1500 rpm (800×g) for 10 min.
7. Remove supernatant and tap tube at the pellet to loosen.
8. Add 15 ml of DMEM-HT. Mix.
9. Transfer to 75 cm² flask. Place in incubator.
10. Add media to cells when it begins to turn orange. Need between $1-3\times10^8$ cells for each fusion depending upon the size of the spleen. Cells should be in log phase at the time of fusion; just slightly orange, which is approximately $5\times10^5$/ml. This means that a minimum of 200 ml of cells are required for a fusion.

Fusion Procedure
Removal of Spleen
1. The mouse should be anesthetized by carbon dioxide gas and bled by cardiac puncture. The mouse is euthanized by cervical dissolocation.
2. The mouse is sprayed with 70% ethanol or isopropanol and placed in a BSC.
3. Using sterile scissors and forceps, the skin is cut on the side below the spleen (left side of mouse). The forceps are used to pull back the skin and hair towards the head.
4. Rinse the scissors and forceps with alcohol. Cut an incision the body cavity to expose the spleen.
5. Use new sterile small forceps and small scissors to remove the spleen. Place in a tube containing Hank's balanced salts solution (minus Ca and Mg). Place tube on ice.

Preparation of PEG
1. If the PEG is presterilzed, place it in a beaker of water that is on a hot plate. The water should not cover the top of the PEG vial. Heat the water to the PEG melts. If the PEG is not sterilized, weigh out 1 g of PEG and place it in 13×100 mm screw cap glass tube. Autoclave for 30 min on slow exhaust.
2. Cool PEG by placing it in a beaker with water in a 37 C water bath.
3. Add 1 ml of warm DMEM-HT for each gram of PEG to the PEG. Place back in water bath.

Place all media and sterile water in 37 C water bath.

Preparation of Lymphocytes
1. Place DMEM-HT in 37 C water bath prior to starting.
2. In BSC, place screen mesh in bottom half of 6 cm Petri dish.
3. Place spleen with Hank's in lid of Petri dish.
4. Use sterile scissors and forceps to trim fat and connective tissue from the spleen.
5. Transfer the spleen to the Petri dish containing the screen. Add DMEM-HT to the dish. Use 1 transfer pipet full.
6. Use the top of the plunger of a 3 or 5 cc syringe to push and grind the spleen into the screen. This breaks the spleen into single cells and small pieces.
7. Lift up the screen and wash it DMEM using a transfer pipet. Set screen aside.
8. Use a transfer pipet transfer the spleen cells to a 50 ml tube. Rinse the Petri dish with DMEM and transfer to the tube.
9. Allow debris to settle to bottom of the tube. Using a transfer pipet, transfer the supernatant to a new 50 ml tube. Add DMEM to 40 ml. Discard debris tube.
10. Centrifuge spleens cells 10 min at 1500 rpm (800×g).
11. Pour off supernatant. Tap bottom of tuber to loosen pellet. Add 10 ml of DMEM-HT. Remove 100 µl for counting. Add 30 ml of DMEM-HT to 50 ml tube containing spleen cells and centrifuge again as above.
12. While centrifuging, take 10 µl of cells and mix with 90 µl of trypan blue. Count cells in one large square of a hemocytometer. Calculate total cells by multiplying the count by $10^6$.
13. Pour off supernatant. Tap bottom of tuber to loosen pellet. Add 40 ml of DMEM-HT. Centrifuge as above with X63 cells from step 3 below.
14. Remove spleen cells from centrifuge. Pour off supernatant. Tap bottom of tuber to loosen pellet. Add 40 ml of DMEM-HT. Centrifuge as above along with X63 cells in step 5 below.
15. Remove spleen cells from centrifuge. Pour off supernatant. Tap bottom of tuber to loosen pellet. Add 10 ml of DMEM-HT. These cells get transferred to the tube containing the X63 cells in step 1 of the fusion protocol.

Preparation of X63 Cells
1. Combine X63 cells into 1 flask. Remove 100 µl for counting.
2. Add 100 µl of trypan blue to 100 µl of X63 cells. Place in hemocytometer and count 1 large square. Determine cells/ml by multiplying the count by $2\times10^4$.
3. Using the total spleen cell count from step 12 in section above calculate the volume required to have the same number of cells as spleen cells.
4. Place the volume of cells in an appropriate number of 50 ml tubes. Centrifuge in the same run as step 13 of the spleen cell procedure.
5. Pour off supernatant. Tap bottom of tuber to loosen pellet. Add 5-10 ml of DMEM-HT depending upon the number of tubes. Combine cells into one tube with 40 ml of DMEM-HT. Centrifuge in the same run as step 14 of the spleen cell procedure.
6. Pour off supernatant. Tap bottom of tuber to loosen pellet. These cells get transferred to the tube containing the spleen cells in step 1 of the fusion protocol.

Fusion Protocol
All media should be at 37 C.
1. Combine spleen cells and X63 cells in the same tube. Add DMEM-HT to 40 ml.
2. Centrifuge at 800 rpm (400×g) for 10 min. Aspirate supernatant.
3. Place sterile 250 ml glass beaker in BSC. Add 100 ml of warm sterile water to beaker.
4. Place tube with pellet in the water.
5. Place PEG/DMEM in BSC. Using a 1 ml pipet, pipet 1 ml of PEG.
6. Add PEG to pellet slowly over 1 min with stirring. The tube is held in the beaker of water.
7. Stir for 1 more min.
8. Using a 1 ml pipet, add 1 ml DMEM-HT over 1 min with stirring.
9. Using a 1 ml pipet, add another 1 ml DMEM-HT over 1 min with stirring.
10. Over the next 2-3 min, add 7 ml of DMEM-HT with a 10 ml pipet with stirring.
11. Centrifuge at 800 rpm (400×g) for 10 min. Aspirate supernatant.
12. Label 3 96 well flat bottom plates during the centrifugation.
13. Add 10 ml of DMEM-20% FBS-HT by releasing in directly on the pellet while stirring. There may be large clumps of cells. This is fine.
14. Add 20 ml of DMEM-20% FBS-HT and swirl the tube to resuspend cells. Do not shake too hard, try to breakup clumps.

15. Using a transfer pipet, distribute 0.1 ml per well. This is approximately 2 drops. This should fill 3 plates. Do not use yellow tips. The hole is too small and may disrupt the fused cells.

Feeding Schedule

Day 0—Fusion day

Day 1—Add 0.1 ml of DMEM-HAT

Days 2, 3, 5, 8, 11—
1. Remove 0.1 ml media per well with a 12 channel pipettor and sterile yellow tips. Place spent media in a sterile basin. The same tips can be used.
2. Place approximately 35 ml of DMEM-HAT in another sterile basin. Add 0.1 ml media per well with a 12 channel pipettor and sterile yellow tips. The same tips can be used.
3. Assay when the media in the wells starts to turn orange/yellow. You may need to feed some individual wells sooner than the schedule. The assay may also need to be done sooner than the schedule. Remove 0.1 ml/well as in feeding and place in assay plate. Add 0.1 ml of DMEM-HAT per well.
4. When viewed under the phase-contrast microscope, there should be dieing spleen and non-fused X63 cells. There should also be foci of fused cells that increase with time. They look similar to the X63 cells that have not been exposed to HAT. They are both attached to the bottom and in suspension.
5. If the cells are growing very fast, transfer them to 24 well plates. Use autoclaved glass Pasteur pipets. The rubber bulbs are soaked in 70% ethanol. 0.4 ml DMEM-HAT is added. This can be increased to 1 ml and then 2 ml of DMEM-HAT.
6. The cells can be further transferred to 6 well plates, which can take up to 10 ml media. The cells should be frozen and cloned from these plates.
7. The cells can be slowly switched to DMEM-HT after transfer to the 24 well plates if desired.

Testing of Antibody Production by ELISA

To prove the proper antibody production and select the wells for further growing and cloning lipid and protein ELISAs were done (high cholesterol liposome w/o lipid-A, cholesterol, DMPC, DMPG and gp140).

Lipid ELISAs. The lipid ELISA was generally performed in accordance with the methods described in:

Alving, B. M., Banerji, B., Fogler, W. E. and Alving, C. R. Lupus anticoagulant activities of murine monoclonal antibodies to liposomal phosphatidylinositol phosphate. Clinical and Experimental Immunology 69 403-408 (1987), incorporated by reference, or, Swartz, Jr., G. M., Gentry, M. K., Amende, L. M., Blanchette-Mackie, E. J. and Alving, C. R. Antibodies to cholesterol. Proceedings of the National Academy of Sciences, U.S.A. 85 1902-1906 (1988). Incorporated by reference with specific details given below.

100 µl of cholesterol (5 nmol/well), DMPC (1 nmol/well), DMPG (10 nmol/well) diluted in ethanol and 100 µl of high cholesterol-DMPC-DMPG liposome diluted in PBS were added into each well of Immulon 2HB U bottom ELISA plate (Thermolab Systems) and allowed to dry in a hood overnight. The cholesterol and liposome plates were blocked with 250 µl of blocking buffer (0.3% gelatin in PBS) and the DMPC, DMPG plates were blocked with 250 µl of 3% BSA for 2 hours. Culture supernatant (50 µl) of each of the hybridomas was added to the plate at room temperature for 2 hours. Plates were washed 5 times with washing buffer (20 mM Tris-HCl pH 7.4, 154 mM NaCl) using an automated plate washer (Seltron MAPC) and exposed to the secondary antibodies as goat anti-mouse IgM antibody conjugated to HRP (Zymed Labs) and sheep affinity-purified and HRP-linked anti-mouse IgG antibody (Binding Site Inc.) for 1 hour. Plates were washed, exposed to ABTS peroxidase substrate system (KPL) at room temperature for 1 hour and then read at 405 nm with Spectra max 250 (Molecular Devices).

Protein ELISA 0.1 ug of gp41, gp120 and gp140 diluted in 100 ul of PBS was added to each well of Immulon 4HBX plates (Thermolab Systems) and allowed to dry in a hood overnight. The plates were blocked with 250 µl of blocking buffer (0.5% casein and 0.5% BSA) for 2 hours. Culture supernatant of the given hybridomas was added to the plate at 4° C. for overnight incubation. Plates were washed 5 times with washing buffer (0.1% Tween-PBS) using an automated plate washer (Seltron MAPC) and exposed to the secondary antibodies for 1 hour. Plates were washed, exposed to the substrate at room temperature for 1 hour and then read.

Cloning

Cloning was done twice by limiting dilution, and the clones were then tested by ELISA.

Figure 2:
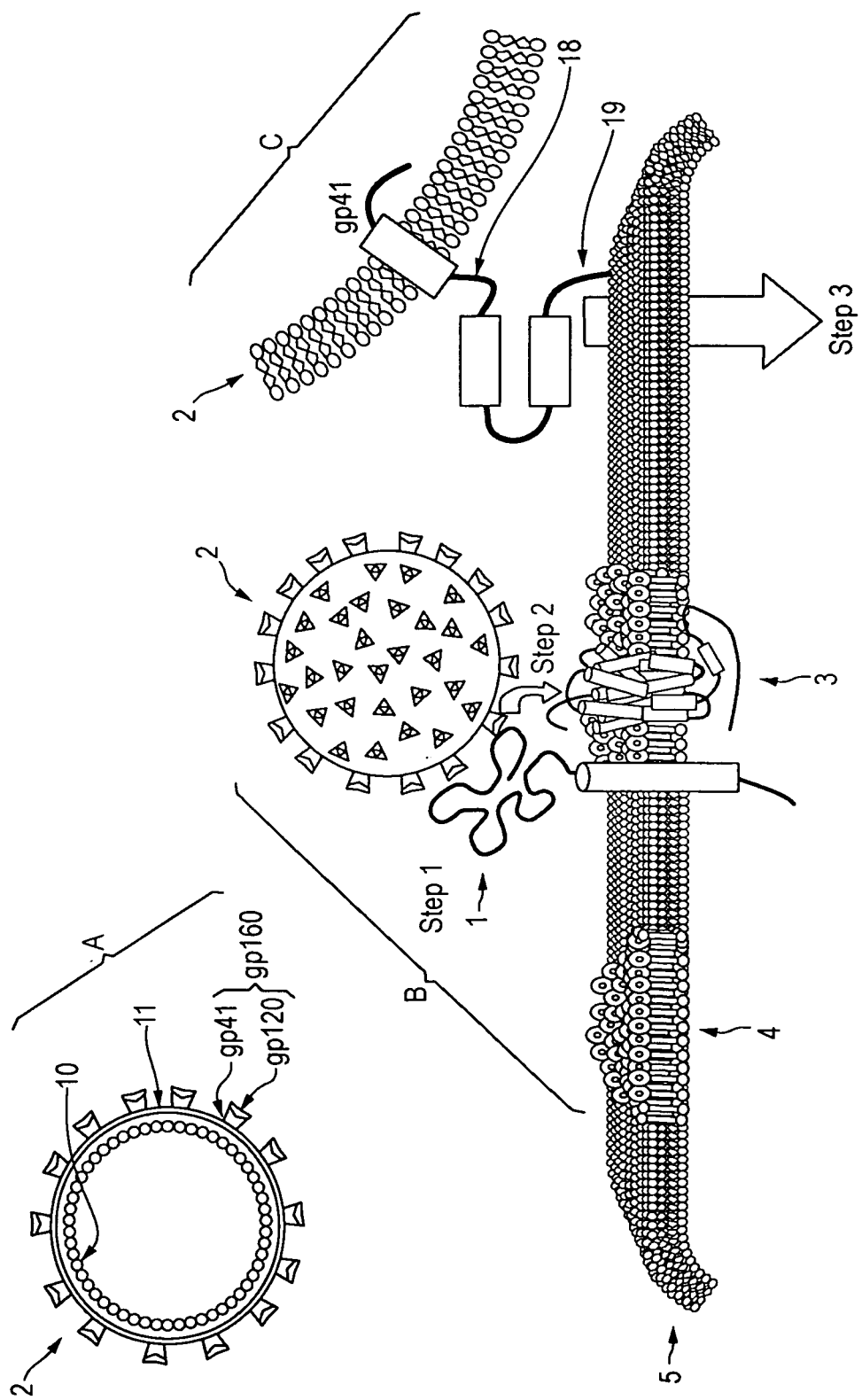
FIG. 2 is a diagram of the interactions of HIV-1 envelope proteins with plasma membrane lipids during target cell binding (B) and fusion steps (C)
Figure 3:
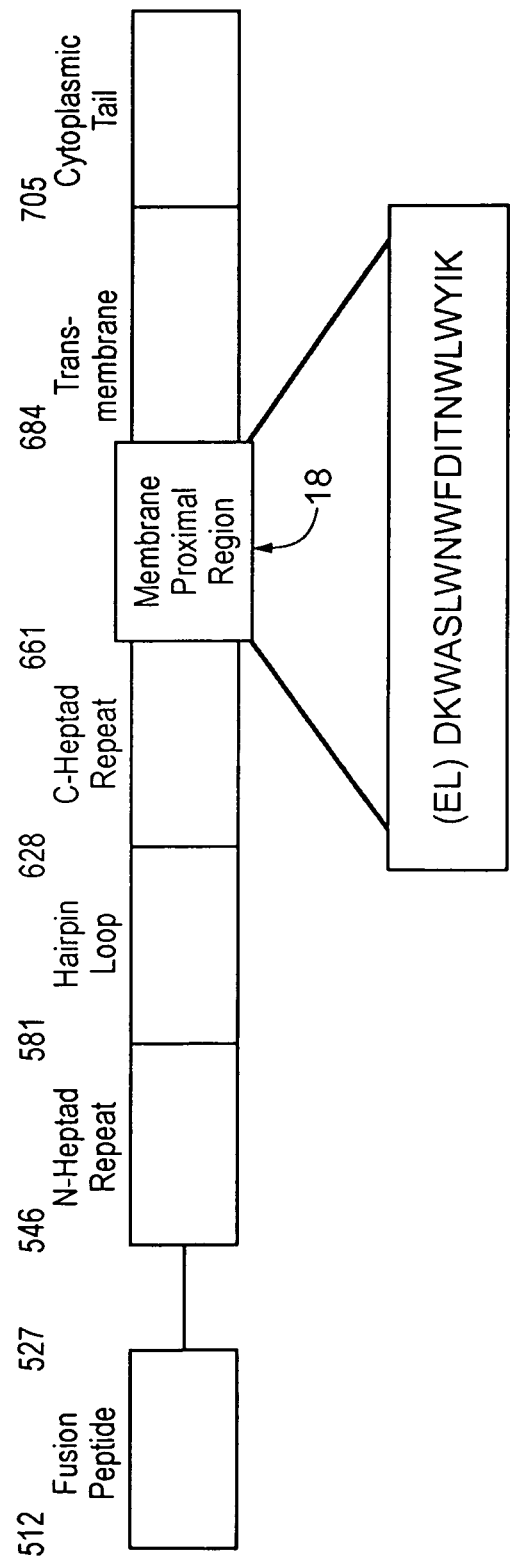
FIG. 3 is a schematic diagram of HIV-1 gp 41 envelope protein (SEQ ID NO: 1)
Figure 4:
FIG. 4 is a model of the HIV-1 molecule showing gp 41 at the vicinity of the lipid bilayer.
Figure 5A:
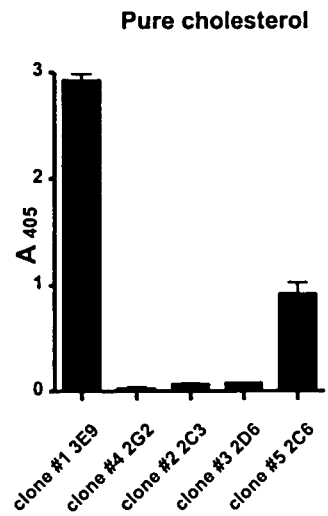
FIGS. 5a, b, c, d, and e are graphs showing the binding of five different clones and their recognition capabilities as shown by ELISA and made by the method of this invention.
Figure 5B:
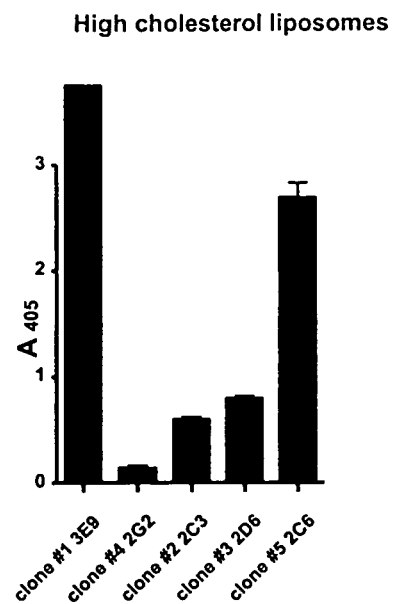
Figure 5C:
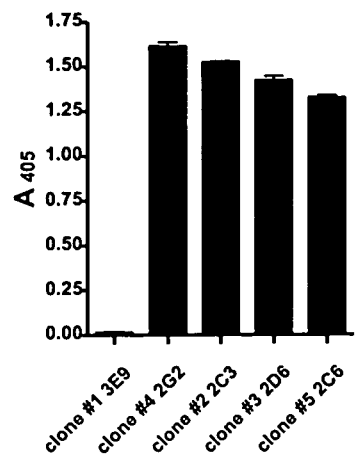
Figure 5D:
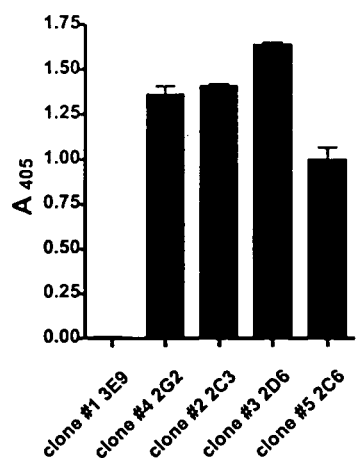
Figure 5E:
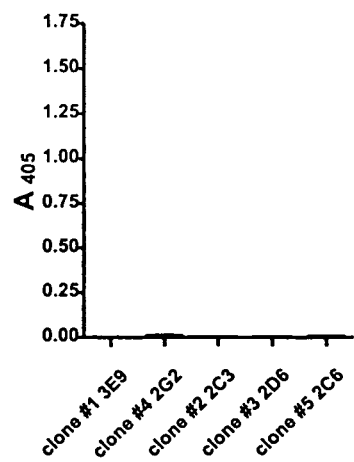
Figure 6A:
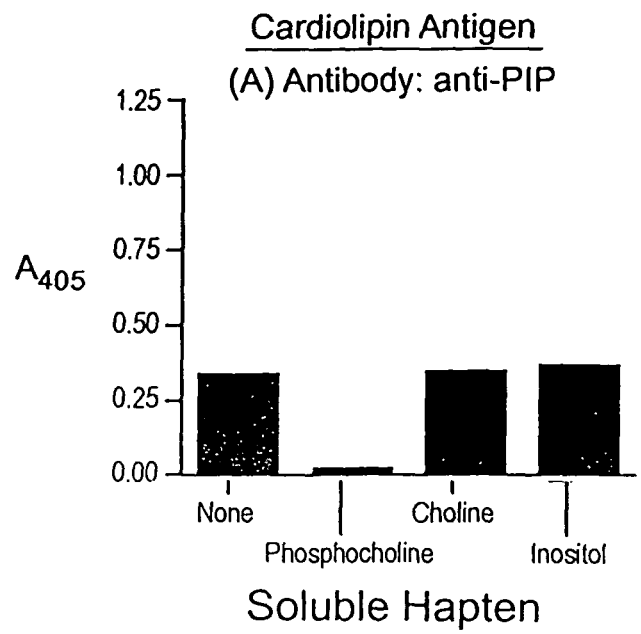
FIGS. 6a and 6b are graphs showing the binding of anti-PIP and 4E10 antibodies, respectively, to CL as determined by ELISA and the effects on bindings by soluble haptens.
Figure 6B:
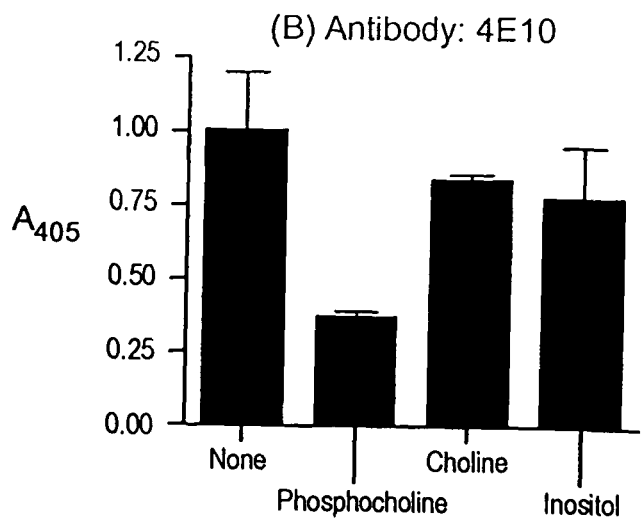
Figure 7A:
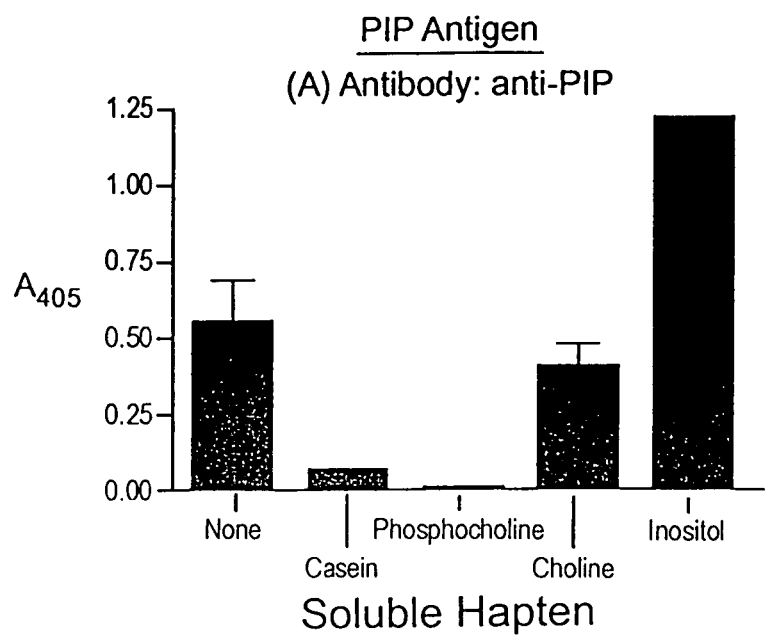
FIGS. 7a and 7b are graphs showing the binding of anti-PIP and 4E10 antibodies, respectively, to PIP antigens as determined by ELISA and the effects on bindings by soluble haptens.
Figure 7B:
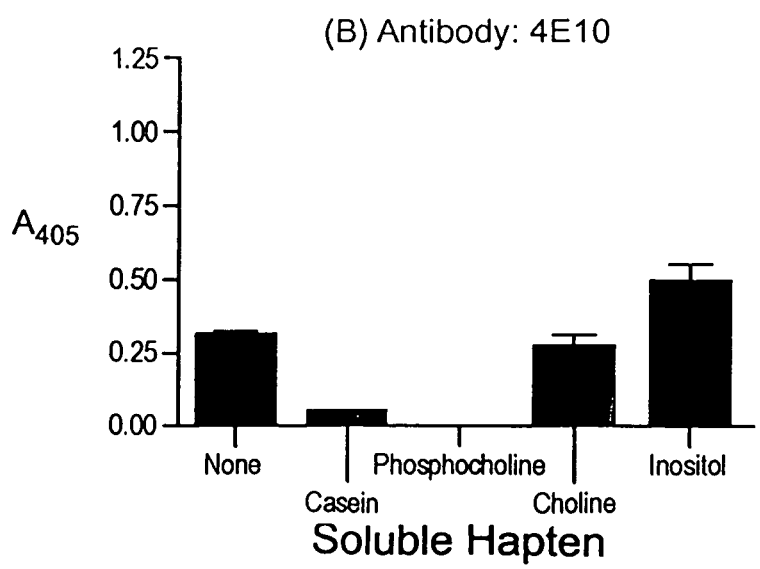

The MPR region 18 of gp41 as shown in FIGS. 2 and 3 contains the binding epitopes for two human IgG monoclonal antibodies that are know to be broadly neutralizing antibodies. They are known as 2F5 and 4E10. 2F5 binds to ELDKWA (SEQ ID NO: 2) (the MPR starts at D) and 4E10 binds to NWFDIT (SEQ ID NO: 3). The 2F5 epitope, ELDKWA (SEQ ID NO: 2), is the same sequence identified as the binding site for GalCer. The cholesterol binding site LWYIK (SEQ ID NO: 4) is at the end of the MPR. The overall series of interactions of HIV-1 involving budding, binding and fusion with host and target cells exposes lipid-associated proteins, and even lipids themselves, as targets for virus neutralization.

The proposed interactions of HIV-1 for fusion with the plasma membrane lipid bilayer lipids are illustrated in FIG. 1. Plasma membrane glycosphingolipid microdomains as preferential sites of formation of the HIV-1 fusion complex. In the plasma membrane of CD4+cells, CD4 1 is present in glycosphingolipid enriched microdomains but is not associated with HIV-1 coreceptors. Once bound to CD4, the viral particle 2 is conveyed to an appropriate coreceptor 3 by the glycosphingolipid raft 4, which moves freely in the external leaflet of the plasma membrane 5, cholesterol 6; glycosphingolipid 4; phosphatidylcholine 7.

As shown in FIG. 2, after budding from host cells, the HIV-1 virus 2 exhibits a strong tendency to infect T lymphocytes as target cells, using CD4 as a receptor 1 (Piguet & Sattentau, 2004). A is a cross section of HIV-1 envelop protein. The binding and fusion of HIV with the target cell involves a choreographed ballet between the proteins of the free virus 2 and the entry site of the target cell (B and C). HIV entry into a cell is a multistep process initially involving the interactions of viral envelope protein gp120 and gp41 with several binding sites on the cell surface. The envelope proteins exist as a trimer consisting of 3 gp120 molecules and 3 gp41 molecules. The binding of gp120 to CD4 is followed by conformational changes in the gp120 protein that expose binding sites to chemokine receptors 3, CXCR4 or CCR5, that serve as co-receptor binding sites for interactions of the virus with the target cell (Berger et al., 1999; Doms, 2000; Huang et al 2005). The binding of gp120 to the chemokine co-receptor in turn induces conformational changes that allow the binding of the gp41 anchor protein to the cell, and this is followed by fusion of the viral lipid bilayer with the plasma membrane bilayer, and entry of the virion RNA into the target cell (Colman & Lawrence, 2003) (C). The binding and entry processes entail numerous types of interactions between proteins and lipids of the virus and specific lipids of the target cell (Fantini et al. 2002).

In FIG. 2, the reference numbers represent as follows: CD4 1, viral particle 2, co-receptor 3, raft 4, plasma membrane 5, p17 matrix 10, lipid bilayer 11, membrane proximal region 18, fusion peptide 19. Also step 3 is fusion and entry.

Humans may be immunized with the appropriate liposomes to produce monoclonal antibodies that have broadly neutralizing activities and a vaccine preparation can be made that would be composed of the above liposomal lipid and protein or peptide combination for testing for protective efficacy against multiple types of HIV clades.

Safety of Antibodies to Lipids Generated by Liposomes Containing Lipid A

Preclinical studies demonstrated that life-long injection of liposomes containing lipid A in mice induced antibodies against numerous lipids, but did not adversely affect the life span of the mice (Richardson et al., 1988-89). Moreover, life-long injection of saline alone into the mice was also associated with age-related appearance of antibodies to lipids, but the antibodies did not appear to have caused any substantive deleterious effects. Liposomes containing lipid A have proven to be extremely safe in numerous phase I and phase II experimental human vaccine trials involving more than 200 volunteers. A high level of safety was observed even with very high concentrations of lipid A (Fries et al., 1992; Heppner et al., 1996; McElrath, 1995; Harris et al., 1999). In the 15 years that such clinical trials have been conducted there have been no reported instances of association of the antibodies with APS or any other autoimmune disease.

Under normal circumstances liposomes themselves are generally not considered immunogenic in experimental animals. However, by utilizing lipid A as an adjuvant in the lipid bilayer liposomes can be rendered immunogenic, and antibodies to liposomal phospholipids have been experimentally induced in animals (rabbits and mice) (Schuster et al., 1978; reviewed by Alving, 1986). By using lipid A, which is the lipid moiety of Gram-negative lipopolysaccharide (endotoxin), as an adjuvant, polyclonal and monoclonal antibodies to liposomal phospholipids (also referred to as anti-phospholipid antibodies, or aPLs) (Banerji et al., 1982; Wassef et al., 1984); liposomal cholesterol (Swartz et al., 1988), and even liposomal squalene (an alkene precursor of cholesterol) (Matyas et al., 2000) have been developed.

Liposomes containing lipid A form the basis of the numerous proposed experimental liposomal vaccines against diseases as diverse as malaria (*Plasmodium falciparum*) (Fries et al., 1992), HIV (McElrath, 1995; Rao et al., 2004; Richards et al., 2004), Ebola hemorrhagic fever (Rao et al., 2002), ricin intoxication (Matyas and Alving, 1996), prostate cancer (Harris et al., 1999; Alving, 2002), and breast cancer (Samuel et al., 1998; Batenjany et al., 2001). In addition to production of antibodies to liposome-encapsulated protein antigen that is present in the vaccine formulation, it is possible that antibodies to the liposomal lipids could also be induced by such vaccines. Considerable evidence indicates that numerous types of circulating antibodies to lipids occur naturally in virtually all normal humans and these antibodies generally do not pose any recognized clinical risk.

Further, humans produce circulating antibodies against such fundamental elements as lipids in the lipid bilayers or tissues of all mammalian cells but do not attack and damage those cells. This is because normal cells are protected from the binding of antibodies to lipids by steric hindrance from adjacent larger molecules.

EXAMPLES

The inventor has shown that certain types of liposomes have been shown to be synthetic models of stabilized lipid raft-like structures and immunological studies with liposomes provide insights about interactions of HIV-1 with lipid bilayers. The inventor found that HIV-1 lipid structures, or liposomes, are useful either as antigens, or as auxiliary lipids in combination with proteins and peptides and have exploited them for immunological approaches to HIV-1 and produced the following results as described in Examples 1 and 2. The following examples are presented to illustrate the invention but it is not to be considered as limited thereto.

Example 1

Antibodies have been produced that have subsite specificities both for lipid and amino acid epitopes and that will bind simultaneously to the lipids and the lipid-associated protein. Mice were immunized with liposomes containing lipid A and containing encapsulated protein from the envelope of HIV-1. A unique murine monoclonal-antibody has now been generated that simultaneously recognizes both the envelope protein by itself, and also recognizes the protein-free liposomes by themselves. In addition, each of the antibodies reacts with at least one individual constituent (cholesterol or high cholesterol liposomes, respectively) that was present in the immunizing liposomes. This demonstrates that the production of unique antibodies having such dual specificities can indeed be produced. Studies to determine whether this antibody has neutralization activity against clinical isolates of HIV-1 are currently being undertaken.

This work has resulted in immunization with synthetic liposomal lipid rafts containing gp140, and the identification and creation of three clones that recognize both gp160 and either dimyristoyl phosphatidylglycerol or cholesterol, or both as shown in FIGS. 5*a*, 5*b*, 5*c*, 5*d* and 5*e*.

FIGS. 5*a*-5*e* demonstrate the binding of five different clones that recognize either lipid alone (cholesterol, or high cholesterol liposomes) or protein (gp41 and gp140, but not gp120), or dual specificity for both lipid and protein, as indicated.

The immunization consisted of the high cholesterol liposomes that contained encapsulated gp140. The gp140 protein consists of a protein that contains both gp120 and part of gp41; thus, the dual specific antibodies were specifically directed only to the gp41 portion of the gp140, and not to the gp120 portion.

| Clone number | Specificity |
|---|---|
| 1 | Cholesterol, and high cholesterol liposomes (i.e., lipid only) |
| 2 | gp41 and gp140 (i.e., protein only) |
| 3 | High cholesterol liposomes, gp41, and gp140 (i.e., lipid and protein) |
| 4. | High cholesterol liposomes, gp41, and gp140 (i.e., lipid and protein) |
| 5. | Cholesterol, high cholesterol liposomes, gp41, and gp140 (i.e., lipid and protein) |

*High Cholesterol liposome is a liposome with a cholesterol content of over 50%. The data as shown has had the low nonspecific background activities in the ELISA subtracted.

These clones have, therefore, tentatively been found to bind to the mpr region of the gp 140, i.e. gp 41, they therefore, might have properties that are similar to 2F5 or 4E10. Numerous other clones have also been identified which have the dual or multi-specific binding specificities defined above. These further clones were obtained after immunizing with synthetic lipid rafts containing phosphatidylinositol phosphate and mpr24, or V3 loop (P18) peptide together with galactosylceramide. The results from these tests are positive.

Example 2

Murine Monoclonal Antibody to Phosphatidylinositol Phosphate (PIP)

Figure 8A:
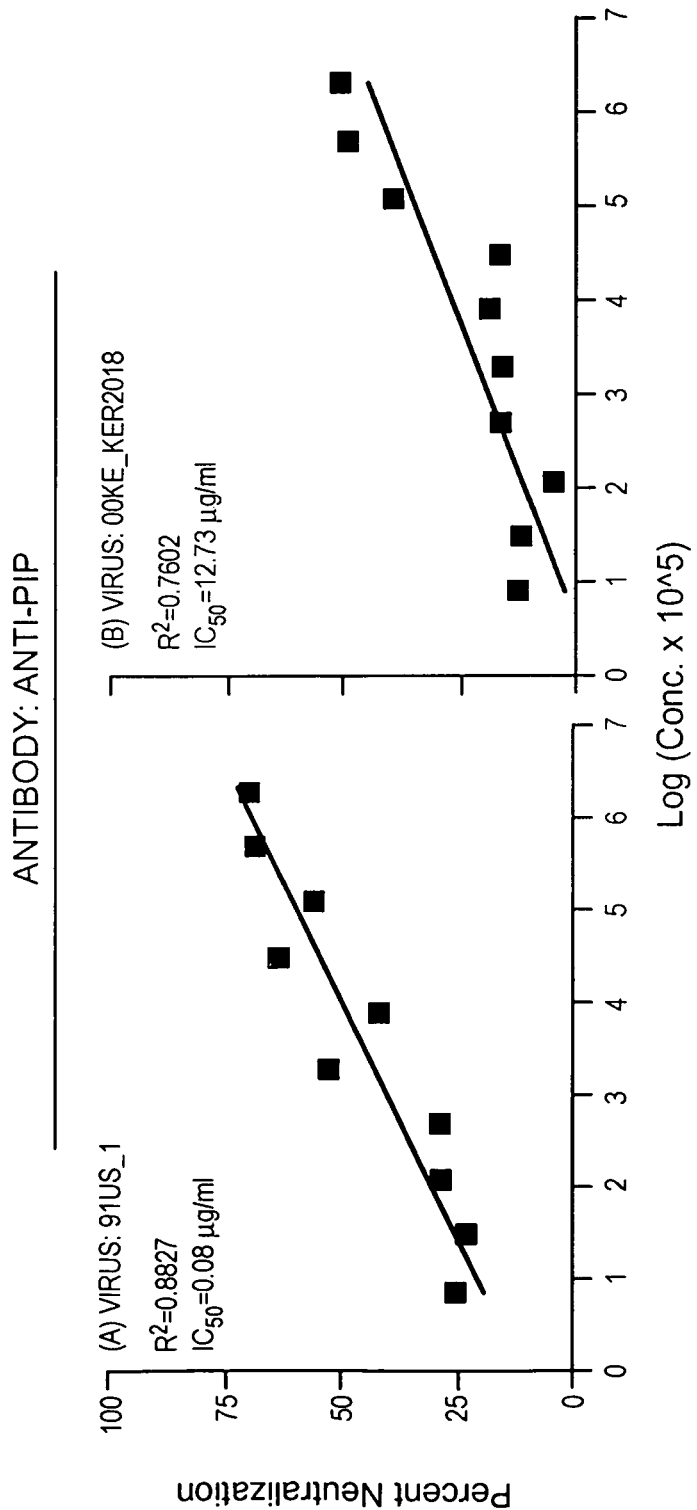
FIG. 8a is a graph showing anti PIP antibody neutralizing activity.
Figure 8B:
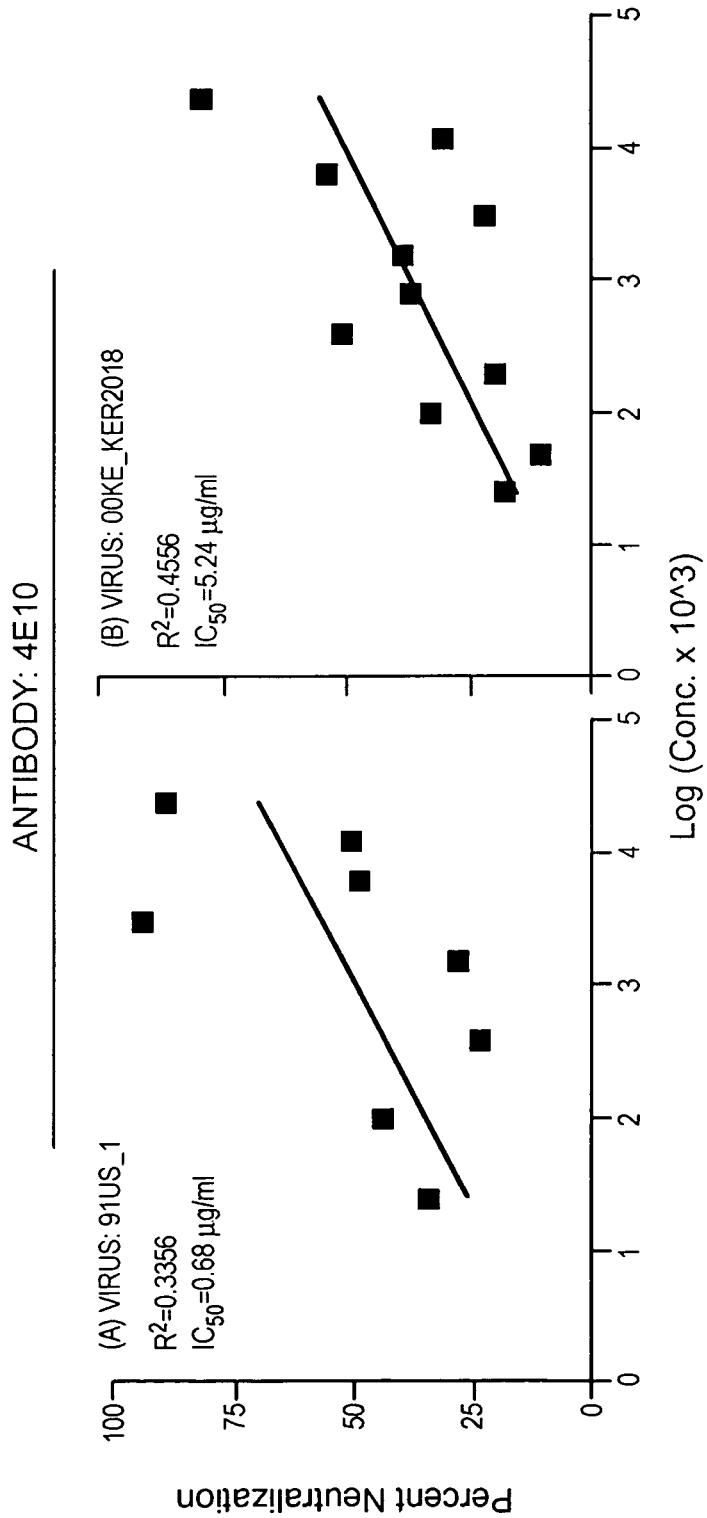
FIG. 8b is a graph showing 4E10 antibody neutralizing activity.

HIV-1 neutralizing capabilities of mabs to PIP have been tested. Antibodies to PIP have the ability to cross-react with cardiolipin which is useful for testing the concept that antibodies to cardiolipin can have broad neutralizing properties for HIV. Extensive experiments have now demonstrated that monoclonal antibodies to PIP do exhibit neutralizing activities against two clinical field isolate strains of HIV-1.

The murine monoclonal antibody to phosphatidylinositol phosphate (PIP) has been shown by the inventor to bind to PIP, as determined by ELISA. This anti-PIP antibody has been shown to have similar binding properties to human monoclonal antibody (4E10). Each of the antibodies had antigen subsite binding specificities in aqueous medium for small phosphate-containing molecules and for inositol. The anti-PIP monoclonal antibody inhibited infection by two HIV-1 clinical isolates in neutralization assays employing primary human peripheral blood mononuclear cells. The data suggest that PIP or related lipids having free phosphates could serve as targets for neutralization of HIV-1.

Recently, an important observation was made that two broadly neutralizing human MAbs, known as 4E10 and 2F5, which are known to react with gp41 of HIV-1 envelope protein, cross-reacted with cardiolipin (CL) and are in the category of antibodies that have lupus anticoagulant-type anti-CL specificities. This observation is also consistent with a previous finding that HIV-1 could bind to, and fuse with, CL liposomes, and that such binding inhibited infection of A3.01 cells by HIV-1. The latter result suggested that HIV-1 has a binding site for CL. The results from the two laboratories could be interpreted as indicating that CL might serve as a binding site for HIV-1 and that interference with the binding to CL could be exploited for vaccine development. However, balanced against this, it is known that CL is not present as a lipid constituent of either HIV-1 or of the plasma membrane of any mammalian cell, and this therefore raises the question whether an alternative lipid antigen might actually be the real neutralizing, and perhaps more important, target of 4E10 and 2F5.

The inventor found that specific polyclonal and monoclonal antibodies to phosphatidylinositol-4-phosphate (PIP) can be readily induced in mice by injection of liposomes containing PIP as an antigen and lipid A as an adjuvant (Alving 1986). Four complement-fixing murine monoclonal antibodies to PIP, selected for their ability to react with liposomes containing PIP but not with liposomes lacking PIP, have been extensively studied (Alving 1987, Alving 1980, Alving 1986, Folger 1987, Friedman 1982, Stollar 1989, Wasseff 1993). The anti-PIP antibodies are characterized by the ability to react with varied types of phosphorylated molecules, including certain closely related anionic phospholipids that have charged non-zwitterionic phosphate groups, such as CL (Alving 1987), and also with denatured DNA (Stollar 1989). Presumably because of cross-reactivity with CL, anti-PIP antibodies gave positive results in clinical assays for lupus anticoagulant activity (Alving 1987). Anti-PIP antibodies can be inhibited by small soluble phosphorylated molecules, such as inositol hexaphosphate (but not inositol), phosphocholine (but not choline), and nucleotides (but not nucleosides) (Alving 1987, Wassef 1993, Stollar 1989). Because of the phosphate-binding subsite that allows such haptenic inhibition to occur, the antibodies can actually serve as high affinity carriers and donors for biologically important molecules, as shown by ability of ATP bound to anti-PIP antibodies to serve as a high energy phosphate donor for an enzymatic (hexokinase) reaction.

In addition to providing information about the molecular architecture of antigen binding subsites, Mabs to PIP are useful probes for exploring potentially important biological binding and receptor activities. Anti-PIP antibodies bind directly to membrane phospholipid on adherent but not on nonadherent macrophages. There is also evidence that PIP can be expressed on the cell surface and act as a receptor for diphtheria toxin. Antibodies to PIP inhibited diphtheria toxin-induced CHO cell cytotoxicity. In view of this, the inventor investigated the potential role that antibodies to PIP might play in the identification of target phospholipid antigens for induction of effective neutralizing antibodies to HIV. It was demonstrated that not only does the 4E10 antibody resemble anti-PIP antibodies in that it binds to PIP and can be inhibited by small phosphorylated molecules, but specific monoclonal anti-PIP antibodies also resemble 4E10 in that they neutralize strains of HIV-1, including two field isolates of HIV-1.

Murine monoclonal IgM antibodies to PIP were obtained after immunizing mice with liposomes containing PIP as an antigen and lipid A as an adjuvant, as previously described. IgM antibody was purified from ascites fluid containing anti-PIP antibody no. 4 by using the protocol supplied with the ImmunoPure IgM Purification kit and Slide-A-Lyser dialysis cassettes (Pierce Chemical Co., Rockville, Ill.). Activities of the anti-PIP and 4E10 antibodies were assayed by ELISA, with slight modification. Monoclonal antibody 4E10 was obtained through the NIH AIDS Research and Reference Reagent Program. The methods for isolation, propagation, and titration of HIV-1 isolates, and the neutralization assay, were used as previously described.

FIGS. 6*a*, 6*b* and 7*a*, 7*b* illustrate the binding of anti-PIP and 4E10 antibodies to CL and PIP, as determined by ELISA, and the effects on binding in the presence of soluble molecules containing free phosphate groups or inositol. The phosphate binding subsite of anti-PIP is revealed by the ELISA data in that casein, a highly phosphorylated protein was inhibitory to binding of anti-PIP both to PIP and to cardiolipin, as was phosphocholine, but no inhibition was found with choline (FIGS. 6*a*,6B). The recently reported binding of the 4E10 antibody to CL is confirmed by our data (FIG. 7*a*), and a new specificity of binding of 4E10 to PIP was also observed (FIG. 7*b*). The 4E10 antibody, as with anti-PIP, has a similar phosphate-binding subsite in that the binding to CL and PIP was inhibited by phosphocholine but not by choline (FIG. 7*a*,7*b*).

The binding of the anti-PIP and 4E10 antibodies to PIP was not inhibited by soluble haptenic inositol (FIG. 7*a*, 7*b*), and inositol actually enhanced the binding of the antibodies to the antigen (FIG. 7*a*, 7*b*). No enhancement was observed in the binding of the antibodies to CL in the presence of inositol (FIG. 6*a*, 6*b*). Separate experiments suggested that the enhancement of binding of the antibodies to PIP, but not to CL, probably reflects a low affinity hydroxyl-hydroxyl association of inositol with the polyhydroxyl headgroups on PIP, combined with low affinity inositol subsites in the anti-PIP and 4E10 antibodies.

The murine anti-PIP monoclonal antibody was examined for possible HIV-1 neutralizing activity in a model utilizing inhibition of infection of primary cultures of peripheral blood mononuclear cells. As shown in FIGS. 8a (A) and (B), the anti-PIP antibody exhibited neutralizing activity that blocked infection of PBMCs by both HIV strain 91US_1 (FIG. 8a (A)) and 00KE_KER2018 (FIG. 8a (B)), both of which are primary clinical isolate strains of HIV-1. Interestingly, when the antibodies were tested against pseudoviruses from multiple clades in the TZM-b1 cell line model system, the 4E10 antibody exhibited neutralization, but the anti-PIP antibody did not neutralize (data not shown). Blinded independent confirmation of the neutralizing activity of the anti-PIP antibody for blocking 91US_1 infection of primary PBMCs (both with PBMCs from the donor shown in FIG. 8a (A) and with PBMCs independently obtained from a separate donor) was kindly provided by Dr. John Mascola at the Vaccine Research Center, NIH (data not shown).

Our data with murine Mab anti-PIP and human Mab 4E10, each of which bind to PIP and CL and neutralize HIV-1, suggest that cell-surface or viral PIP, or related inositol phosphatides, could play a role in the interaction of HIV-1 with target cells. The inositol phosphatides, which comprise a family of eight chemical species with different combinations of phosphate groups arranged around the polyhydroxyl inositol ring, are highly versatile signaling molecules, with key roles in receptor-mediated signal transduction, signal-induced actin assembly and remodeling, and membrane trafficking PIP, an intermediate in the synthesis of phosphatidylinositol-4,5-bis-phosphate (PIP2) from phosphatidylinositol, is synthesized by a PI-4-kinase that is located in the lipid rafts and caveolae-like vesicles of the plasma membrane of eukaryotic cells. A huge and sometimes confusing array of proteins bind to inositol phosphatides, perhaps the most well-known of which are glycosylphosphatidylinositol (GPI)-anchored proteins. Certain GPI-anchored proteins, such as Thy-1 and CD59, are incorporated into the HIV-1 virion during budding of the virus from lipid rafts. GPI-anchored proteins were originally discovered on the surface of *Trypanosoma brucei*, and antibodies to PI and PIP were induced in rabbits infected with *Trypanosoma rhodesiense*). Thus, PIP in an infectious organism can be immunogenic, and it appears possible that PIP in the lipid bilayer of the HIV-1 virion or in the host cell, or other membrane lipids with free phosphate, could represent a target for neutralizing antibodies to HIV-1. Regardless of the exact mechanism of neutralization by anti-PIP and 4E10 antibodies, it does appear evident that the phosphate binding subsite, and possibly the inositol-binding subsite, of each antibody might play a role. The data suggest that the neutralizing effects of anti-PIP, and perhaps 4E10, may be more strongly associated with the headgroups of the phospholipids than with hydrophobic interactions with the hydrophobic regions of either HIV-1 or plasma membrane lipid bilayers.

ELISA Technique for PIP and Cardiolipin.

The ELISA procedure was developed by modification of previous techniques for analysis of antibody binding to lipid antigens (Smolarsky 1980; Loizou et al. 1985). PI, PS, or CL was coated onto the surface of wells in polystyrene microtitre plates (Immunolon I, 'U" bottom, Dynatech Labs Inc., Alexandria, Va.) by addition of an ethonolic solution and evaporation of the solvent by air under a fume hood. Plates were further dried under high vacuum and stored at −20° C. when not used the same day. Plates were blocked by addition of phosphate-buffered saline (PBS), pH 7.2, containing 0.3% gelatin (Difco Laboratories, Detroit, Mich.). This was accomplished by washing the wells three times for 5 min each with PBS containing 0.3% gelatin. Fifty microliters of goat anti-mouse IgM (μ chain specific) alkaline phosphatase conjugate (Kirkegaard and Perry Laboratories, Inc. Gaithersburg, Md.) at μg/ml in PBS containing 1% BSA were added to the wells and incubated for 30 min. at 22° C. Plates were agains washed three times for 5 min each with PBS containing 0.3% geletan. Fifty microliters of the substrate p-nitrophenylphosphate at an initial concentration of 2 mg/ml in diethanolamine buffer 9Kirkegaard and Perry Laboratories, Inc.) were added to the wells and incubated for 30 Min at 22° C. Plates were scanned for optical activity at 405 nm with Titertek Multiscan (Flow Laboratories, McLean, Va.). Values reported were adjusted by substracting values in wells that lacked monoclonal antibody. Alving (1987)

Example 3

The inventor's further goal was to achieve a vaccine that would cover numerous clades, so they considered sequences that are highly conserved. Two such conserved antigenic regions are portions of the mpr region of gp41 and the lipid bilayer itself, including lipids such as phosphatidylinositol phosphate, phosphatidylserine, phosphatidylglycerol, and cholesterol. Additionally, certain conserved regions in gp120, particularly conserved elements of the V3 loop, are known to bind to glycolipids, including galactosyl ceramide and ganglioside GM3.

The inventor has shown that a monoclonal antibody may be produced that has successfully neutralized two field isolates of HIV-1 and a further monoclonal antibody that has been generated that simultaneously recognizes both a protein (gp160 from HIV) and one or more protein-free liposomal lipids. It would be understood by one of ordinary skill in the art that this method of producing a dual specific monoclonal antibody that recognizes both an amino acid sequence and a lipid epitope can be applied to other substances other than HIV-1. Other substances or entities to be neutralized are other viruses, bacteria, hormones, fungi, cancer cells, protozoa or any other entity that triggers an antibody immune response.

DEFINITIONS

4E10, 2F5, and Z13: These are designations of monoclonal antibodies, derived from individual humans infected with HIV-1, or that have been identified from phage display libraries, that have the ability to broadly neutralize clinical isolates of HIV-1. The antibodies are further taught and described by Buchacher et al. [Buchacher A, Predi R, Strutzenberger K, Steinfellner W, Trkola A, Purtscher M, Gruber G, Tauer C, Steindl F, Jungbauer A, Katinger H. Generation of human monoclonal antibodies against HIV-1 proteins; electrofusion and Epstein-Barr virus transformation for peripheral blood lymphocyte immortalization. AIDS Research and Human Retroviruses. April 1994; 10(4):359-369] and by Zwick et al. [Zwick M B, Labrijn A F, Wang M, Spenlehauer C, Saphire E O, Binley J M, Moore J P, Stiegler G, Katinger H, Burton D R, Parren P W, Broadly neutralizing antibodies targeted to the membrane-proximal external region of human immunodeficiency virus type 1 glycoprotein gp41. Journal of Virology November 2001; 75(22): 10892-10905].

Adjuvant: An adjuvant is defined as anything that will amplify the immune response or improve the immune response over what the immune response would be without the adjuvant.

Antigenic epitope (or, more simply, an epitope): Molecular recognition site for binding of antibodies. Commonly this is determined or produced by injecting an antigenic material into a mammal, or by introduction of the antigenic material to lymphocytes in vitro, for presentation of the antigenic material to lymphocytes to induce antibodies that are secreted by lymphocytes, and said antibodies then have the capacity to bind to sites on the material that had been presented to the lymphocytes.

Broadly neutralizing: A commonly encountered problem in HIV-1 immunology and vaccinology is the inability of antibodies induced against HIV-1 organisms produced in the laboratory to prevent (i.e., neutralize) primary isolates of HIV-1 viruses from infecting target cells. Broadly neutralizing antibodies are defined as antibodies that have the ability to partially or completely overcome this problem by neutralizing more than one type of primary isolate of HIV-1 virus.

Enveloped virus: A virus that has an envelope (i.e., an outer lipid bilayer structure together with associated proteins on the outer surface) is an enveloped virus. Examples of such viruses include: HIV-1, influenza virus, dengue virus, Sindbis virus, and Ebola virus, among many others.

Dual-specific or multi-specific: This is defined as the ability of the antigen binding site of an antibody to bind simultaneously or independently to epitopes on two or more types of antigenic chemical species, for example to an amino acid sequence and to a lipid; or to a sugar and a lipid; or to an amino acid sequence and a sugar. The term "dual" refers only to binding to more than one type of chemical epitope, but such antibody binding specificities may actually contain as many molecular binding sub-sites for different types of chemical epitopes (including three, or more, epitopes) as there is available space on the antigen binding site of the antibody for such simultaneous binding of more than one type of epitope.

Lipid: Lipids are defined as taught by Small, D. M., "The Physical Chemistry of Lipids, From Alkanes to Phospholipids" Handbook of Lipid Research, Vol, 4, Plenum, N.Y., 1986, p. 1, as given below:

"1.1 Definition of lipids: Assuming a broad definition, one can define a lipid as any molecule of intermediate molecular weight (between 100 and 5000) that contains a substantial portion of aliphatic or aromatic hydrocarbon. Included are the hydrocarbons, steroids, soaps, detergents, and more complex molecules, such as triacylglycerols, phospholipids, gangliosides, and lipopolysaccharides. Immediately, one can imagine that the physical behavior of such chemically divergent molecules will be quite different. Indeed one of the most interesting characteristics of lipids is their tremendously varied behavior in aqueous systems, ranging from almost total insolubility (e.g., paraffin oil and sterol esters) to nearly complete solubility (e.g., soaps, detergents, bile salts, and gangliosides). This particular aspect of lipids is important biologically because all cells exist in an aqueous milieu."

Lipid structure (this includes all organized lipid structures, or domains, and all solid phase, mesomorphic, crystalline, liquid crystalline, and liquid lipid structures): This is defined as all of the multiple organized physical states of lipids, as taught by Small, D. M., in "The physical states of lipids: solids, mesomorphic states, and liquids" in "The Physical Chemistry of Lipids, From Alkanes to Phospholipids" Handbook of Lipid Research, Vol, 4, Plenum, N.Y., 1986, Chapter 3, pp. 43-87. All of the above terms are interchangeable as defined in the context of this invention. Thus, the term "solid phase lipid structure" is interchangeable with "mesomorphic states", "liquid lipids", "organized lipid structures" "domains", "crystalline lipid structures", liquid crystal lipid structures", and "liquid lipid structures".

Lipid bilayer membrane: This is a type of double layer membrane in which the polar groups of the parallel array of lipids of each monolayer of lipids are oriented toward the aqueous phase and the nonpolar groups (such as fatty acyl groups) of each monolayer are oriented toward each other in the center of the bilayer. Liposomes often contain lipid bilayers, as do plasma membranes of cells.

Liposomes: Liposomes, as they are ordinarily used, consist of smectic mesophases, and may consist or either phospholipid or nonphospholipid smectic mesophases.

Definition of "Smectic Mesophase" as taught by Small, D. M., in "The Physical Chemistry of Lipids, From Alkanes to Phospholipids" Handbook of Lipid Research, Vol, 4, Plenum, N.Y., 1986, pp. 49-50 is given below:

"When a given molecule is heated, instead of melting directly into an isotropic liquid, it may instead pass through intermediate states called mesophases or liquid crystals, characterized by residual order in some directions but by lack of order in others . . . . In general, the molecules of liquid crystals are somewhat longer than they are wide and have a polar or aromatic part somewhere along the length of the molecule. The molecular shape and the polar-polar, or aromatic, interaction permit the molecules to align in partially ordered arrays . . . . These structures characteristically occur in molecules that possess a polar group at one end. Liquid crystals with long-range order in the direction of the long axis of the molecule are called smectic, layered, or lamellar liquid crystals . . . . In the smectic states the molecules may be in single or double layers, normal or tilted to the plane of the layer, and with frozen or melted aliphatic chains."

Primary isolates of HIV-1: These are isolates of HIV-1 that are found spontaneously in human populations. Commonly, such isolates are obtained from clinical specimens taken from individuals naturally infected with HIV-1. Primary isolates differ from laboratory isolates in that the latter are strains of HIV-1 that are adapted to growth in transformed T cell lines.

Other bonding specificities of the antibodies of the invention are also contemplated. In addition to making dual specific antibodies, multi-specific antibodies for binding two or more antigenic epitopes are within the scope of the invention. These other antigenic epitopes include combinations of two or more amino acid sequences, lipids, sugars, and carbohydrates.

The invention has been described herein with reference to certain preferred embodiments. However, as obvious variations thereon will become apparent to those skilled in the art, the invention is not to be considered as limited thereto.

REFERENCES

Aloia, R. C., Jensen, F. C., Curtain, C. C., Mobley P. W., Gordon, L. M., (1988) Lipid composition and fluidity of the human immunodeficiency virus. Proc Natl Acad Sci USA 85:900-904.

Aloia, R. C, Tian, H., and Jensen, F. C. (1993) Lipid composition and fluidity of the human immunodeficiency virus envelope and host cell plasma membranes. Proc. Natl. Acad. Sci. U.S.A. 90:5181-5185.

Alving, B. M., Banerji, B., Folgler, W. E., and Alving C. R. (1987) Lupus anticoagulant activities of murine monoclonal antibodies to liposomal phosphatidylinositol phosphate, Clin. Exp. Immunol. 69:403-408.

Alving, C. R., Iglewski, B., Urban, K. A., Moss, J., Richards, R. L., and Sadoff, J. C., (1980) Binding of diphtheria toxin to phospholipids in liposomes. Proc. Natl. Acad. Sci., U.S.A. 77: 1986-1990.

Alving, C. R. (1986) Antibodies to liposomes, phospholipids, and phosphate esters. Chem Phys Lipids 40:303-314.

Alving, C. R. (2002) Design and selection of vaccine adjuvants: Animal models and human trials, Vaccine 20:S56-S64.

Banerji, B., Lyon, J. A., Alving, C. R. (1982) Membrane lipid composition modulates the binding specificity of a monoclonal antibody against liposomes. Biochim Biophys Acta, 689:319-326.

Batenjany, M. M., Boni, L. T., Guo, Y., Neville, M. E., Bansal, S., Robb, R. J., Popescu, M. C. (2001) The effect of cholesterol in a liposomal Muc 1 vaccine. Boichem Biophys Acta 1514:280-290.

Berger, E. A., Murphy P. M. Farber, J. M. (1999) Chemokine receptors as HIV-1 coreceptors: roles in viral entry, tropism, and disease. Annu Ref Immunol. 17:657-700.

Callahan, M. K., Popernack, P. M., Tsutsui, S., Truong, L., Schlegel R. A., Henderson, A. J., (2003) Phosphatidylserine on HIV envelope is a cofactor for infection of monocytic cells. J. Immunol. 170:4840-4845.

Chernomordik, L., Chanturiya, A. N., Suss-Toby, E., Nora, E., Zimmerberg, J. (1994) An amphipathic peptide from the C-terminal region of the human immunodeficiency virus envelope glycoprotein causes pore formation in membranes. J Virol. 68:7115-7123.

Colman, P. M., Lawrence, M. C. (2003) The structural biology of type I viral membrane fusion. Nat Rev Mol Cell Biol 4:309-319.

Domas, R. W. (2000) Beyond receptor expression: the influence of receptor conformation, density, and affinity in HIV-1 infection. Virology 276:229-237.

Fantini, J., Garmy, N., Mahfoud, R., Yahi, N. (2002) Lipid rafts: structure, function and role in HIV, Alzheimer's and prion diseases, Expert Rev Mol Med 20 December, http://expertreviews.org/02005392h.htm.

Fogler, W. E., Swartz, G. M., Alving, C. R. (1987) Antibodies to phospholipids and liposomes: binding of antibodies to cells. Biochim. Biophys. Acta 903:265-272.

Freed, E. O., Martin, M. A. (1995) Virion incorporation of envelope glycoproteins with long but not short cytoplasmic tails is blocked by specific single amino acid substitutions in the human immunodeficiency virus type 1 matrix. J Virol 69:1984-1989.

Friedman, R. L., Inglewski, B. H., Roerdink, F., Alving, C. R. (1982) Suppression of cytotoxicity of diphtheria toxin by monoclonal antibodies against phosphatidylinositol phosphate. Biophys J 37:23-24.

Fries, L. F., Gordon, D. M., Richards, R. L., Egan, J. E., Hollingdale, M. R., Gross, M., Silverman, C., Alving, C. R. (1992) Liposomal malaria vaccine in humans: A safe and potent adjuvant strategy. Proc. Natl. Acad. Sci. USA 89:358-362.

Harris, D. T., Matyas, G. R., Gomella, L. G., Talor, E., Winship, M. D., Spitler, L. E., Mastrangelo, M. J. (1999) Immunologic approaches to the treatment of prostate cancer. Semin. Oncology 26:439-447.

Heppner, D. G., Gordon, D. M., Gross, M., Wellde, B., Leitner, W., Krzych, U., Schneider, I., Wirtz, R. A., Richards, R. L., Trofa, A., Hall, T., Sadoff, J. C., Boerger, P., Alving, C. R., Sylvester, D. R., Porter, T. G., Ballou, W. R. (1996) Safety, immunogenicity and efficacy of *Plasmodium falciparum* repeatless circumsporozoite protein vaccine encapsulated in liposomes, J. Infect. Dis. 174-361-366.

Hill, C. P., Worthylake, D., Bancroft, D. P., Christensen, A. M., Sundquist, W. I. (1996) Crystal structures of the trimeric human immunodeficiency virus type 1 matrix protein: Implications for membrane association and assembly. Proc Natl Acad Sci USA 93:3099-3104.

Huang, C. C., Tang, M., Zhang, M-Y., Majeed, S., Montabana, E., Stanfield, R. L., Dimitrov, D. S., Korber, B., Sodroski, J., Wilson I. A., Wyatt, R., Kwong, P. D. (2005) Structure of a V3-containing HIV-1 gp120 core., Science 310:1025-1028.

Matyas, G. R., Wasser, N. M, Rao, M., Alving, C. R. (2000) Induction and detection of antibodies to squalenel, J Immunol Methods 245:1-14.

McElrath, M. J. (1995) Selection of potent immunological adjuvants for vaccine construction. Semin Cancer Biol. 6:375-385.

Piguet, V., Sattentau, Q. (2004) Dangerous liaisons at the virological synapse. J Clin. Invest 114:605-610.

Rao, M., Bray, M., Alving, C. R., Jahrling, P., Matyas, G. R. (2002) Induction of immune responses in mice and monkeys to Ebola virus after immunization with liposome-encapsulated irradiated Ebola virus: protection I mice requires CD4+ T cells. J. Virol., 76:9176-9185

Rao, M., Matyas, G. R., VanCott, T. C., Birx, D. L., Alving, C. R. (2004) Immunostimulatory CpG motifs induce cytotoxic T lymphocytes responses to human immunodeficiency virus type I oligomeric gp140 envelope protein. Immunol. Cell Biol. 82-523-530.

Richards, R. L., Rao, M., VanCott, T. C., Matyas, G. R., Birx, D. L., Alving, C. R. (2004) Liposome-stabilized oil-in-water emulsions as adjuvants: increased emulsion stability promotes induction of cytotoxic T lymphocytes against an HIV envelope antigen. Immunol. Cell Biol. 82:531-538.

Richardson, E. C., Swartz, Jr., G. M., Moe, J. B., Alving, C. R. (1988-89) Life-long administration of liposomes and lipid A in mice: Effects on longevity, antibodies to liposomes, and terminal histopathological patterns. J. Liposome Res. 1: 93-110.

Samuel, J., Budzynski, W. A., Reddish, M. A., Ding, L., Zimmermann, G. L., Krantz, M. J., Koganty, R. R., Longenecker, B. M. (1998) Immunogenicity and antitumor activity of a liposomal MUC1 peptide-based vaccine. Int. J. Cancer 75-295-302.

Schuster, B., Neidig, M., Alving, B. M., Alving, C. R. (1979), Production of antibodies against phosphocholine, phosphatidylcholine, sphingomyslin, and lipid A by injection of liposomes containing lipid A., J. Immunol. 122:900-905.

Stollar, B. D., McInerney, T., Gavron, T., Wassef, N. M., Swartz Jr., G. M., Alving, C. R. (1989) Cross-reactions of nucleic acids with monoclonal antibodies to phosphatidylinositol phosphate and cholesterol. Mol. Immunol. 26:73-79.

Swartz Jr., G. M., Gentry, M. K., Amende, L. M., Blanchette-Mackie, E. J., Alving, C. R. (1988) Antibodies to cholesterol, Proc Natl Acad Sci USA, 85:1902-1906.

Trommeshauser, D., Krol, S., Bergelson, L. D., Galla, H. J. (2000) The effect of lipid composition and physical state of phospholipids monolayer on the binding and incorporation of a basic amphipathic peptide from the C-terminal region of the HIV envelope protein gp41. Chem Phys Lipids. 107:83-92.

Wassef, N. M., Roerdink, R., Swartz, Jr., G. M., Lyon, J. A., Berson, B. J., Alving, C. R., (1984) Phosphate binding specificities of monoclonal antibodies against phosphoinositides in liposomes., Mol Immunoll, 21:863-868.

Wassef, N. M., Swartz, G. M., Alving, B. M., Alving, C. R. (1993) ATP specifically bound as a hapten to a monoclonal anto-phospholipid antibody retains phosphate donor activity. Biochem. Biophys. Res. Commun. 190:582-588.

Zwick M B, Labrijn A F, Wang M, Spenlehauer C, Saphire E O, Binley J M, Moore J P, Stiegler G, Katinger H, Burton D R, Parren P W. (2001) Broadly neutralizing antibodies targeted to the membrane-proximal external region of human immunodeficiency virus type 1 glycoprotein gp41. J Virol. 75:10892-10905.

What is claimed is:

1. A method of making monoclonal antibodies having specificity for both, the lipid and the lipid associated HIV protein antigen, comprising:
   a) obtaining liposomes having lipid epitopes to HIV-1 and modifying said liposomes by incorporating: (1) an adjuvant and (2) a protein or peptide epitope from HIV-1 virus;
   b) immunizing a mammal with said liposomes;
   c) producing said antibodies, wherein said antibodies have simultaneous recognition subsites to said lipid epitopes in said liposome and to said protein or peptide epitope of said HIV-1 virus;
   d) identifying said antibodies with simultaneous recognition subsites to said lipid epitopes in said liposome and to said protein or peptide epitope of said HIV-1 virus;
   e) isolating only said antibodies with simultaneous recognition subsites to said lipid epitopes in said liposome and to said protein or peptide epitope of said HIV-1 virus; and
   f) cloning said antibodies to obtain monoclonal dual-multi specific antibodies having dual or multi-specific antigen binding sites binding more than one antigenic epitope selected from lipid epitope and an HIB epitope.

2. The method of claim 1, wherein said protein or peptide epitopes from HIV-1 comprise one or more of gp160, gp120, gp 140, and gp41.

3. The method of claim 1, wherein said lipid epitopes comprise one or more of phosphatidylcholine, phosphatidylethanolamine, sphingomyelin, phosphatidylserine, phosphatidylinositol-4-phosphate, phosphatidylinositol, phosphatidyl glycerol, GalCer, SGalCer, CTH, GM1, GM3 and cholesterol.

4. The method of claim 1, wherein said lipid epitopes comprise one or more lipid epitopes found in a lipid raft region of a plasma membrane of a host cell.

5. The method of claim 1, wherein said adjuvant is Lipid A.

6. The method of claim 1, wherein said liposome further comprise nef, either alone or with env antigens.

* * * * *

SEQUENCE LISTING

```
<160> NUMBER OF SEQ ID NOS: 4

<210> SEQ ID NO 1
<211> LENGTH: 22
<212> TYPE: PRT
<213> ORGANISM: Human immunodeficiency virus type 1

<400> SEQUENCE: 1

Glu Leu Asp Lys Trp Ala Ser Leu Trp Asn Trp Phe Asp Ile Thr Asn
 1               5                  10                  15

Trp Leu Trp Tyr Ile Lys
            20

<210> SEQ ID NO 2
<211> LENGTH: 6
<212> TYPE: PRT
<213> ORGANISM: Human immunodeficiency virus type 1

<400> SEQUENCE: 2

Glu Leu Asp Lys Trp Ala
 1               5

<210> SEQ ID NO 3
<211> LENGTH: 6
<212> TYPE: PRT
<213> ORGANISM: Human immunodeficiency virus type 1

<400> SEQUENCE: 3

Asn Trp Phe Asp Ile Thr
 1               5

<210> SEQ ID NO 4
<211> LENGTH: 5
<212> TYPE: PRT
<213> ORGANISM: Human immunodeficiency virus type 1

<400> SEQUENCE: 4

Leu Trp Tyr Ile Lys
 1               5
```